United States Patent
Inouye et al.

(10) Patent No.: US 9,422,599 B2
(45) Date of Patent: Aug. 23, 2016

(54) COLD SHOCK PROTEIN COMPOSITIONS AND METHODS AND KITS FOR THE USE THEREOF

(75) Inventors: Masayori Inouye, New Brunswick, NJ (US); Sangita Phadtare, Highland Park, NJ (US); Ikunoshin Kato, Shiga (JP); Ling Zhu, Hurstville (AU); Hiroyuki Mukai, Shiga (JP); Takashi Uemori, Shiga (JP); Kazue Nishiwaki, Shiga (JP)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 727 days.

(21) Appl. No.: 12/919,985

(22) PCT Filed: Mar. 2, 2009

(86) PCT No.: PCT/US2009/035772
§ 371 (c)(1),
(2), (4) Date: Jan. 4, 2011

(87) PCT Pub. No.: WO2009/108949
PCT Pub. Date: Sep. 3, 2009

(65) Prior Publication Data
US 2011/0097722 A1    Apr. 28, 2011

Related U.S. Application Data

(60) Provisional application No. 61/067,596, filed on Feb. 29, 2008, provisional application No. 61/195,747, filed on Oct. 9, 2008.

(30) Foreign Application Priority Data

May 16, 2008    (JP) .................................. 2008-129745

(51) Int. Cl.
*C12N 9/12*    (2006.01)
*C12Q 1/68*    (2006.01)

(52) U.S. Cl.
CPC .................................. *C12Q 1/6848* (2013.01)

(58) Field of Classification Search
None
See application file for complete search history.

(56) References Cited

U.S. PATENT DOCUMENTS

| 4,889,818 | A | * | 12/1989 | Gelfand et al. | 435/194 |
| 5,500,363 | A | * | 3/1996 | Comb et al. | 435/194 |
| 5,714,575 | A | * | 2/1998 | Inouye et al. | 530/300 |
| 5,998,195 | A | * | 12/1999 | Kacian et al. | 435/252.33 |
| 2003/0113712 | A1 | | 6/2003 | Lee et al. | |
| 2005/0097640 | A1 | | 5/2005 | Fernandes et al. | |
| 2007/0105113 | A1 | | 5/2007 | Sagawa et al. | |

FOREIGN PATENT DOCUMENTS

| JP | H10234389 | 9/1998 |
| JP | 2002153280 | 5/2002 |
| JP | 2003519482 | 6/2003 |
| JP | 3910015 | 2/2007 |
| JP | 2008048746 | 3/2008 |
| WO | 9009444 | 8/1990 |
| WO | 9009447 | 8/1990 |
| WO | 0055307 | 9/2000 |
| WO | 0192500 | 12/2001 |

OTHER PUBLICATIONS

International Search Report for International Patent Application No. PCT/US2009/035772 issued Sep. 21, 2009.
European Search Report for European Patent Application No. 09713748.3 issued Jun. 4, 2011.
Brandi, A. et al., "Interaction of the main cold shock protein CS7.4 (CspA) of *Escherichia coli* with the promoter region of hns," Biochem, Masson, vol. 76, No. 10-11, pp. 1090-1098 (Jan. 1, 1994).
Weining et al., "CspA, the major cold-shock protein of *Escherichia coli*, is an RNA chaperone," Journal of Biological Chemistry, vol. 272, No. 1, pp. 196-202 (1997).
Basu, S. et al., "Execution of macrophage apoptosis by PE_PGRS33 of Mycobacterium tuberculosis is mediated by Toll-like receptor 2-dependent release of tumor necrosis factor-alpha." J Biol Chem, vol. 282, pp. 1039-1050 (2007).
Brennan, M.J. et al., "The PE multigene family: a 'molecular mantra' for mycobacteria." Trends Microbiol, vol. 10, pp. 246-249 (2002).
Chatterjee, S. et al., "The backbone structure of the major cold-shock protein CS7.4 of *Escherichia coli* in solution includes extensive beta-sheet structure." Journal of Biochemistry, vol. 114, pp. 663-669 (1993).
Chon, H. et al., "Site-specific cleavage of MS2 RNA by a thermostable DNA-linked RNase H." Protein Eng, vol. 15, pp. 683-688 (2002).
Delogu, G. et al., "PE_PGRS proteins are differentially expressed by MycobacteriuM. tuberculosis in host tissues." Microbes Infect vol. 8, pp. 2061-2067 (2006).
Denny, P.W. et al., "Rafts and sphingolipid biosynthesis in the kinetoplastid parasitic protozoa." Mol Microbiol, vol. 53, pp. 725-733 (2004).
Dheenadhayalan, V. et al., "Variable expression patterns of Mycobacterium tuberculosis PE_PGRS genes: evidence that PE PGRS 16 and PE PGRS26 are inversely regulated in vivo." J Bacteriol, vol. 188, pp. 3721-3725 (2006).

(Continued)

*Primary Examiner* — Richard Hutson
(74) *Attorney, Agent, or Firm* — Lowenstein Sandler LLP

(57) ABSTRACT

The present invention provides cold shock protein-containing compositions for improved DNA synthesis reactions with improved reactivity, methods for synthesizing DNA using such compositions, kits for use in such methods, and DNA compositions yielded by such methods. The present invention further provides cold shock protein-containing compositions for the identification of endoribonuclease cleavage sites, methods for identifying endoribonuclease cleavage sites using such compositions, and kits for use in such methods.

12 Claims, 41 Drawing Sheets

(56) References Cited

OTHER PUBLICATIONS

Fu, Z. et al., "Characterization of MazFSa, an endoribonuclease from *Staphylococcus aureus*." J Bacterial, vol. 189, pp. 8871-8879 (2007).

Golby, P. et al., "Comparative transcriptomics reveals key gene expression differences between the human and bovine pathogens of the Mycobacterium tuberculosis complex." Microbiology, vol. 153, pp. 3323-3336 (2007).

Inouye, M., "The discovery of mRNA interferases: Implication in bacterial physiology and application to biotechnology." J Cell Physiol, vol. 209, pp. 670-676 (2006).

Jiang, W. et al., "CspA, the major cold-shock protein of *Escherichia coli*, is an RNA chaperone." J Biol Chem, vol. 272, pp. 196-202 (1997).

Mishra, K.C. et al., "The Mycobacterium tuberculosis triacylglycerol hydrolase LipY: functional role of the PE domain and immunogenicity." Infect Inunun., vol. 76, No. 1, pp. 127-140 (2007).

Pandey, D.P. et al., "Toxin-antitoxin loci are highly abundant in free-living but lost from host-associated prokaryotes." Nucleic Acids Res, vol. 33, pp. 966-976 (2005).

Singh, K.K. et al., "Immunogenicity of the Mycobacterium tuberculosis PPE55 (Rv3347c) protein during incipient and clinical tuberculosis." Infect Immun, vol. 73, pp. 5004-5014 (2005).

Suzuki, M. et al., "Single protein production in living cells facilitated by an mRNA interferase." Mol Cell, vol. 18, pp. 253-261 (2005).

Wang, Nan et al., "Cspl, the Ninth Member of the CspA Family of *Escherichia coli*, Is Induced upon Cold Shock." Journal of Bacteriology, vol. 181. No. 5, pp. 1603-1609 (1999).

Zhang, J.et al., "Characterization of the interactions within the mazEF addiction module of *Escherichia coli*."J Biol Chem, vol. 278, pp. 32300-32306 (2003).

Zhang, J. et al., "Interference of mRNA function by sequence-specific endoribonuclease PemK." J Biol Chem, vol. 279, pp. 20678-20684 (2004).

Zhang, Y. et al., "MazF cleaves cellular mRNAs specifically at ACA to block protein synthesis in *Escherichia coli*." Mol Cell, vol. 12, pp. 913-923 (2003).

Zhang, Y. et al., "Insights into the mRNA cleavage mechanism by MnzF, an mRNA interferase." J Biol Chem, vol. 280, pp. 3143-3150 (2005).

Zhang, Y. et al., "Characterization of ChpBK, an mRNA interferase from *Escherichia coli*.." J Biol Chem, vol. 280, pp. 26080-26088 (2005).

Zhu, L. et al., "Characterization of mRNA interferases from mycobacterium tuberculosis." J Biol Chem, vol. 281, No. 27, pp. 18638-18643 (2006).

Schindelin, Hermann et al., "Crystal sructure of CspA, the major cold shock protein of *Escherichia coli*," Proc. Natl. Acad. Sci, USA, vol. 91, pp. 5119-5123, May 1994, Biochemistry, pp. 5119-5123.

Huang, H., et al., "Fidelity and Predominant Mutations Produced by Deep Vent Wild-Type and Exonuclease-Deficient DNA Polymerases During in Vitro DNA Amplification," DNA and Cell Biology, Jul. 1996, vol. 15, No. 7, Mary Ann Liebert, New York, NY, US. Abstract.

Shröder, K, et al., "Mutational analysis of the putative nucleic acid-binding surface of the cold-shock domain, CspB, revealed an essential role of aromatic and basic residues in binding of single-stranded DNA containing the Y-box motif," Molecular Microbiology, May 1995, vol. 15, No. 4, Abstract.

Takahashi, H., et al., "Human immunodeficiency virus type 1 reverse transcriptase: Enhancement of activity by nteraction with cellular topoisomerase I," Proceedings of the National Academy, Jun. 1995, vol. 92, pp. 5694-5698.

\* cited by examiner

A: template DNA = 5ng
B: template DNA = 50ng

A: template DNA = 5ng
B: template DNA = 50ng

A: template DNA = 5ng
B: template DNA = 50ng

1: TP53 gene 575bp
2: Bcl2 gene 591bp
3: EGFR gene 521bp
4: CDK9 gene 380bp
5: FFAR2 gene 1010bp
6: IRS1 gene 520bp
7: GAP gene 460bp 1: TP53 gene   575bp
2: Bcl2 gene   591bp
3: EGFR gene   521bp
4: CDK9 gene   380bp
5: FFAR2 gene 1010bp
6: IRS1 gene   520bp
7: GAP gene    460bp

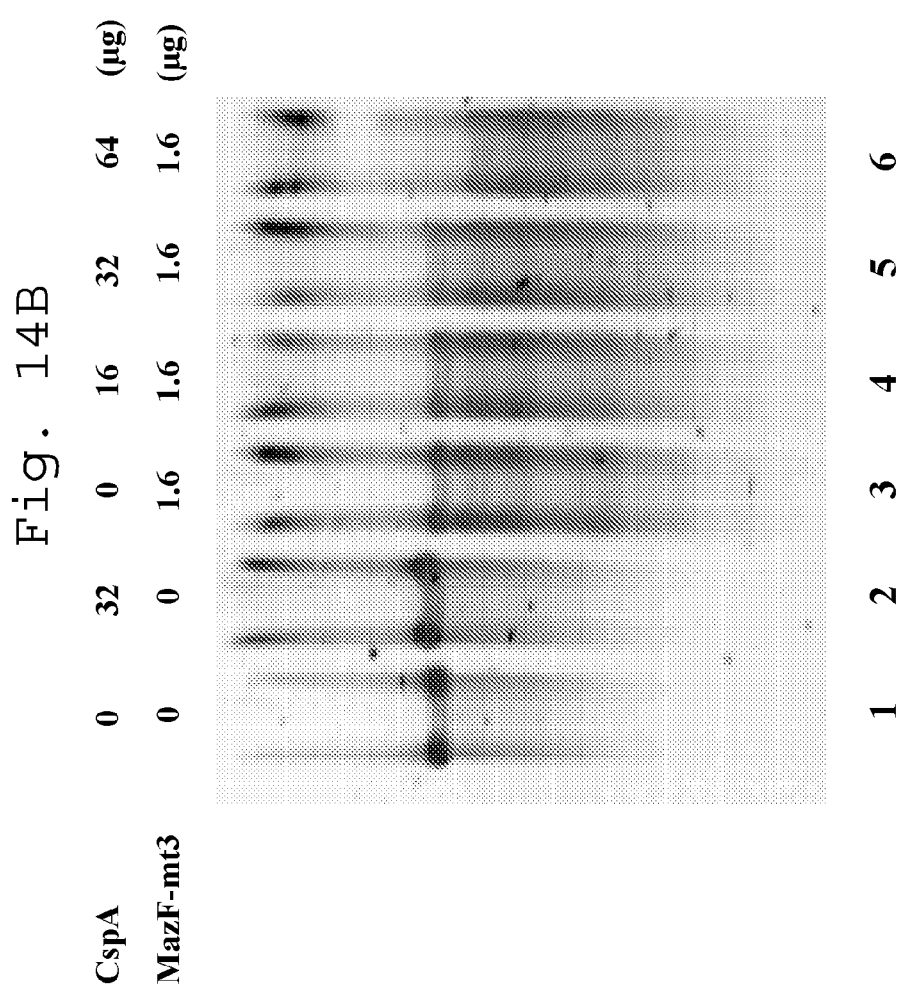

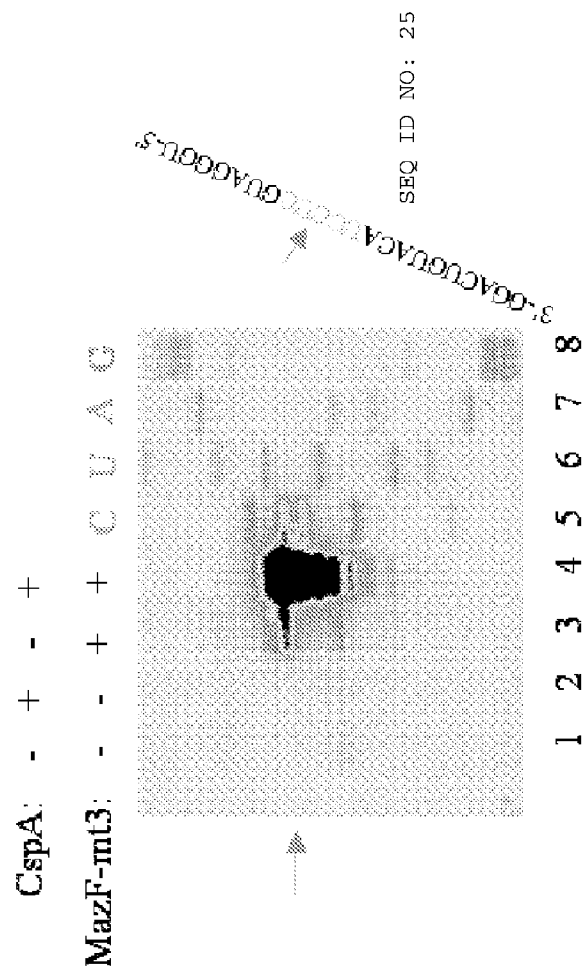

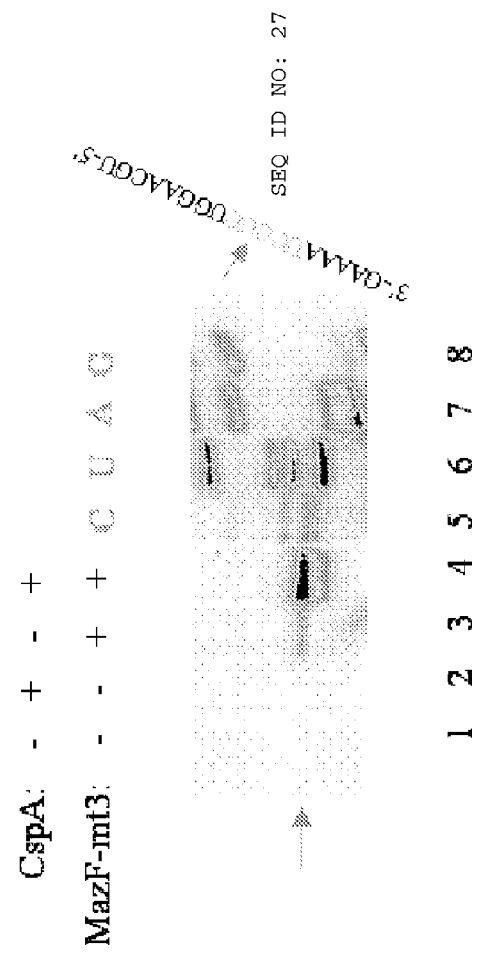

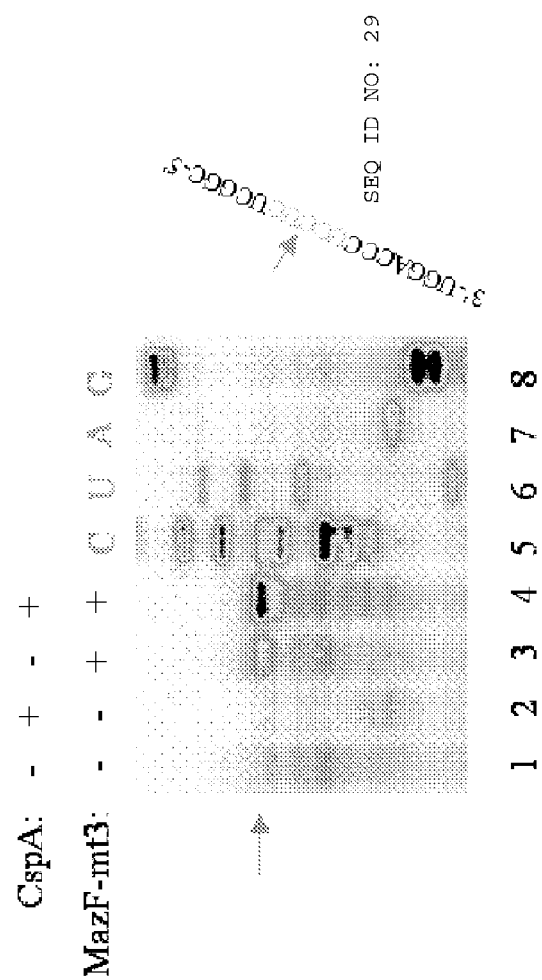

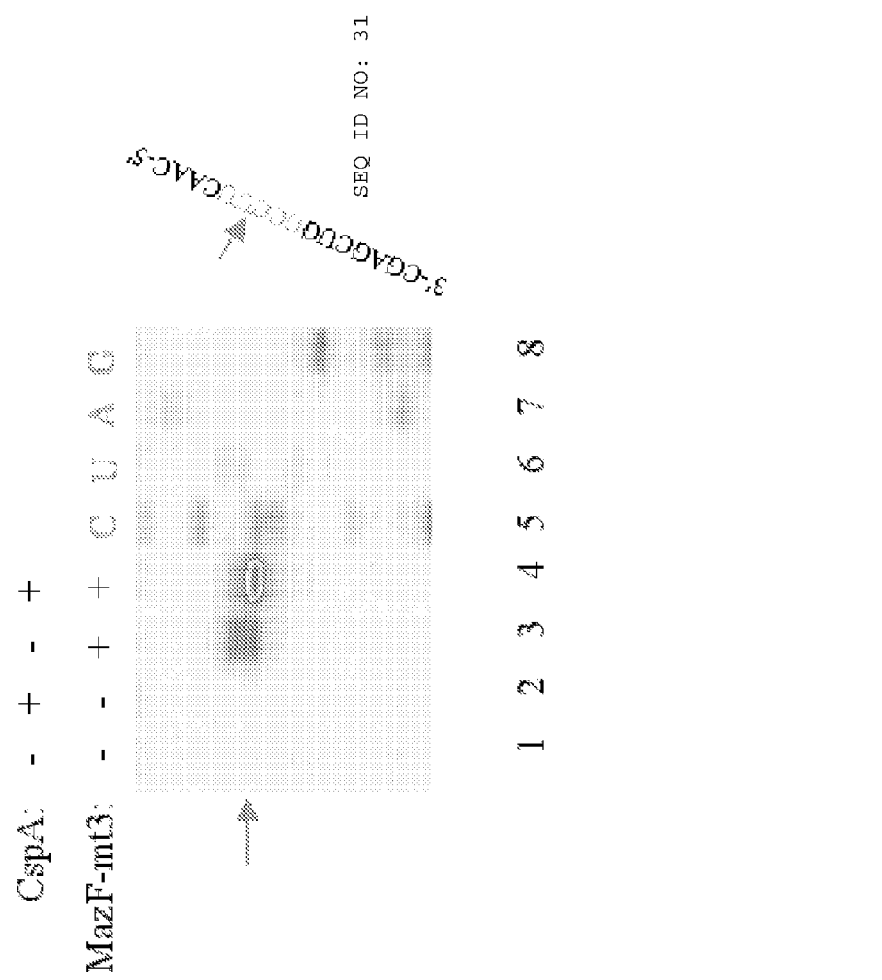

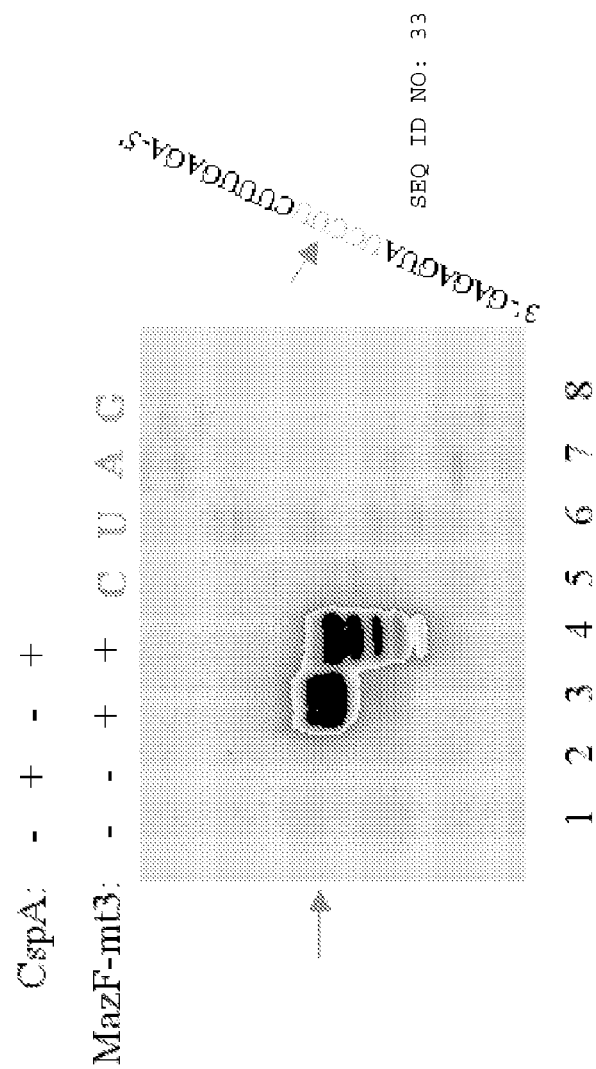

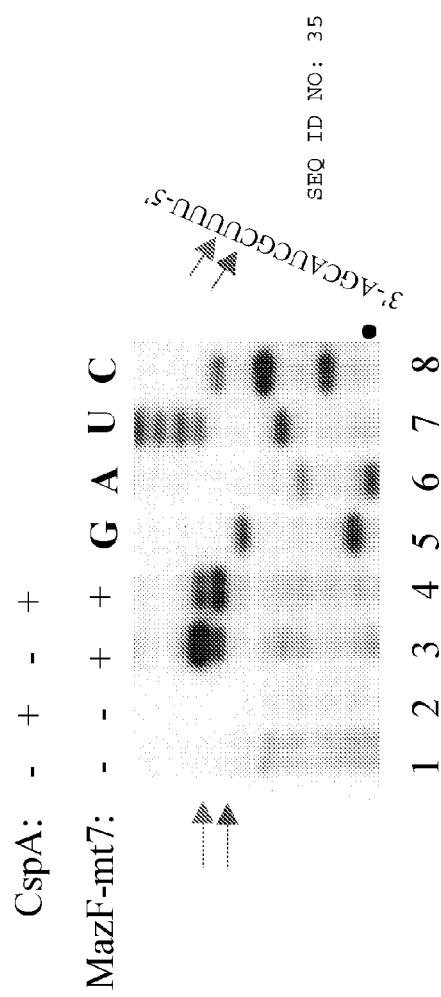

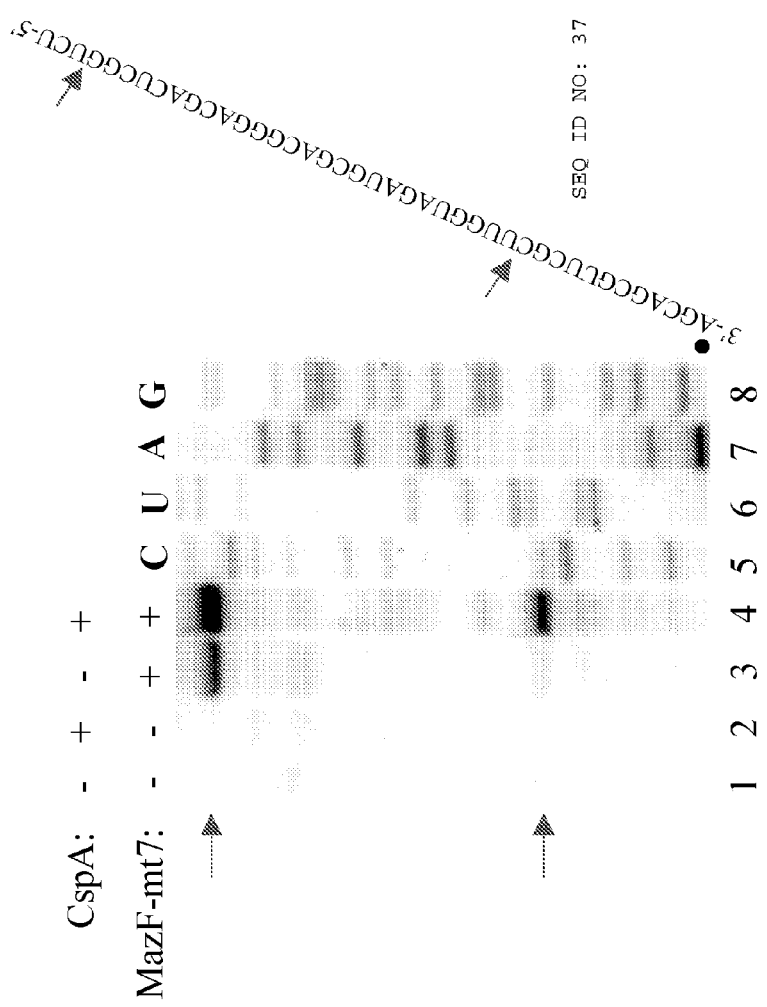

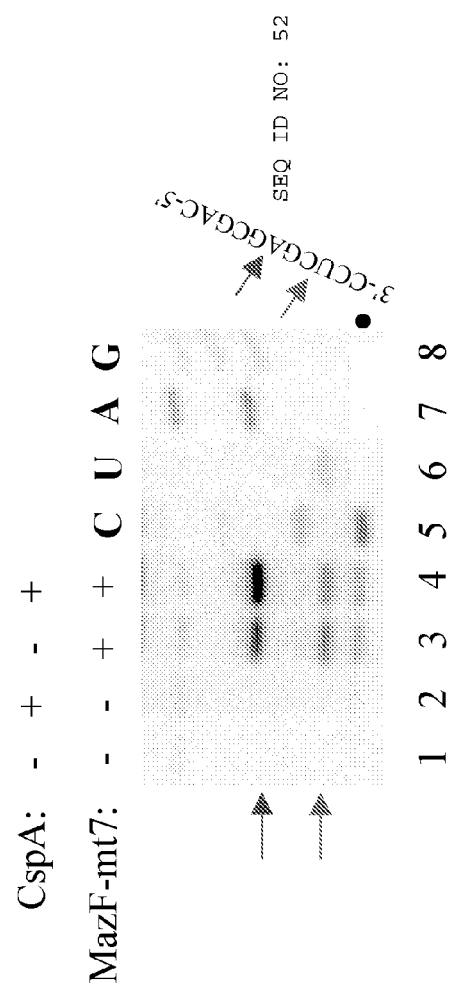

SEQUENCE LISTING

<160> NUMBER OF SEQ ID NOS: 110

<210> SEQ ID NO 1
<211> LENGTH: 25
<212> TYPE: DNA
<213> ORGANISM: Artificial Sequence
<220> FEATURE:
<223> OTHER INFORMATION: Synthetic primer for PCR to amplify of p53 gene

<400> SEQUENCE: 1
ttgtttatgg tgtgaggtgt aggag                                           25

<210> SEQ ID NO 2
<211> LENGTH: 25
<212> TYPE: DNA
<213> ORGANISM: Artificial Sequence
<220> FEATURE:
<223> OTHER INFORMATION: Synthetic primer for PCR to amplify of p53 gene

<400> SEQUENCE: 2
ctagtttgct aggaggttgg ttggt                                           25

```
<210> SEQ ID NO 3
<211> LENGTH: 25
<212> TYPE: DNA
<213> ORGANISM: Artificial Sequence
<220> FEATURE:
<223> OTHER INFORMATION: Synthetic primer for PCR to amplify of TP53
      gene

<400> SEQUENCE: 3
gcagtggctc acgaatccca cactc                                            25

<210> SEQ ID NO 4
<211> LENGTH: 25
<212> TYPE: DNA
<213> ORGANISM: Artificial Sequence
<220> FEATURE:
<223> OTHER INFORMATION: Synthetic primer for PCR to amplify of TP53
      gene

<400> SEQUENCE: 4
tgagtcaggc ccttctgtct tgaac                                            25

<210> SEQ ID NO 5
<211> LENGTH: 25
<212> TYPE: DNA
<213> ORGANISM: Artificial Sequence
<220> FEATURE:
<223> OTHER INFORMATION: Synthetic primer for PCR to amplify of Bcl2
      gene

<400> SEQUENCE: 5
atggcgcacg ctgggagaac agggt                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic primer for PCR to amplify of Bcl2
      gene

<400> SEQUENCE: 6
acctacccag cctccgttat cctgg                                            25

<210> SEQ ID NO 7
<211> LENGTH: 25
<212> TYPE: DNA
<213> ORGANISM: Artificial Sequence
<220> FEATURE:
<223> OTHER INFORMATION: Synthetic primer for PCR to amplify of EGFR
      gene

<400> SEQUENCE: 7
ttcctttcat gctctcttcc ccagg                                            25

<210> SEQ ID NO 8
<211> LENGTH: 25
<212> TYPE: DNA
<213> ORGANISM: Artificial Sequence
<220> FEATURE:
<223> OTHER INFORMATION: Synthetic primer for PCR to amplify of EGFR
      gene

<400> SEQUENCE: 8
ggctacggcg gtgtaggaga tgcca                                            25
```

```
<210> SEQ ID NO 9
<211> LENGTH: 25
<212> TYPE: DNA
<213> ORGANISM: Artificial Sequence
<220> FEATURE:
<223> OTHER INFORMATION: Synthetic primer for PCR to amplify of CDK9
      gene

<400> SEQUENCE: 9
cccaggtgtg gccaaacgtg gacaa                                          25

<210> SEQ ID NO 10
<211> LENGTH: 25
<212> TYPE: DNA
<213> ORGANISM: Artificial Sequence
<220> FEATURE:
<223> OTHER INFORMATION: Synthetic primer for PCR to amplify of CDK9
      gene

<400> SEQUENCE: 10
cgccggccct cagaagacgc gctca                                          25

<210> SEQ ID NO 11
<211> LENGTH: 25
<212> TYPE: DNA
<213> ORGANISM: Artificial Sequence
<220> FEATURE:
<223> OTHER INFORMATION: Synthetic primer for PCR to amplify of FFAR2
      gene

<400> SEQUENCE: 11
ccaggatgct gccggactgg aagag                                          25

<210> SEQ ID NO 12
<211> LENGTH: 25
<212> TYPE: DNA
<213> ORGANISM: Artificial Sequence
<220> FEATURE:
<223> OTHER INFORMATION: Synthetic primer for PCR to amplify of FFAR2
      gene

<400> SEQUENCE: 12
ccagggaaac tgctactctg tagtg                                          25

<210> SEQ ID NO 13
<211> LENGTH: 25
<212> TYPE: DNA
<213> ORGANISM: Artificial Sequence
<220> FEATURE:
<223> OTHER INFORMATION: Synthetic primer for PCR to amplify of IRS1
      gene

<400> SEQUENCE: 13
ggcagcatgg cgagccctcc ggaga                                          25

<210> SEQ ID NO 14
<211> LENGTH: 25
<212> TYPE: DNA
<213> ORGANISM: Artificial Sequence
<220> FEATURE:
<223> OTHER INFORMATION: Synthetic primer for PCR to amplify of IRS1
      gene

<400> SEQUENCE: 14
ccttgggctt caggatcact tgcca                                          25
```

```
<210> SEQ ID NO 15
<211> LENGTH: 25
<212> TYPE: DNA
<213> ORGANISM: Artificial Sequence
<220> FEATURE:
<223> OTHER INFORMATION: Synthetic primer for PCR to amplify of GAP
      gene

<400> SEQUENCE: 15
tggggaggca actaggatgg tgtgg                                           25

<210> SEQ ID NO 16
<211> LENGTH: 25
<212> TYPE: DNA
<213> ORGANISM: Artificial Sequence
<220> FEATURE:
<223> OTHER INFORMATION: Synthetic primer for PCR to amplify of GAP gene

<400> SEQUENCE: 16
caagtcaggg gagcgtgtcc atagg                                           25

<210> SEQ ID NO 17
<211> LENGTH: 20
<212> TYPE: DNA
<213> ORGANISM: Artificial
<220> FEATURE:
<223> OTHER INFORMATION: Synthetic primer for real time PCR
      quantification of dystrophin cDNA.

<400> SEQUENCE: 17
acaagggcga tttgacagat                                                 20

<210> SEQ ID NO 18
<211> LENGTH: 25
<212> TYPE: DNA
<213> ORGANISM: Artificial
<220> FEATURE:
<223> OTHER INFORMATION: Synthetic primer for real time quantification
      of dystrophin cDNA

<400> SEQUENCE: 18
gtatttagca tgttcccaat tctca                                           25

<210> SEQ ID NO 19
<211> LENGTH: 25
<212> TYPE: DNA
<213> ORGANISM: Artificial
<220> FEATURE:
<223> OTHER INFORMATION: Synthetic primer for real time quantification
      of dystrophin cDNA

<400> SEQUENCE: 19
aaaggtccag cgtcacataa aggaa                                           25

<210> SEQ ID NO 20
<211> LENGTH: 24
<212> TYPE: DNA
<213> ORGANISM: Artificial
<220> FEATURE:
<223> OTHER INFORMATION: Synthetic primer to amplify a DNA fragment of
      dystrophin gene.

<400> SEQUENCE: 20
gctcaaatgc ctcaggaagc ccag                                            24
```

```
<210> SEQ ID NO 21
<211> LENGTH: 23
<212> TYPE: DNA
<213> ORGANISM: Artificial
<220> FEATURE:
<223> OTHER INFORMATION: Synthetic primer to amplify a DNA fragment of
      dystrophin gene.

<400> SEQUENCE: 21
aagagtggcc tactccttca cag                                             23

<210> SEQ ID NO 22
<211> LENGTH: 20
<212> TYPE: DNA
<213> ORGANISM: Artificial
<220> FEATURE:
<223> OTHER INFORMATION: Synthetic primer to amplify a DNA fragment of
      dystrophin gene.

<400> SEQUENCE: 22
gcatctctcc taatgagagc                                                 20

<210> SEQ ID NO 23
<211> LENGTH: 13
<212> TYPE: RNA
<213> ORGANISM: Bacteriophage MS2

<400> SEQUENCE: 23
gacaucgucc ucg                                                        13

<210> SEQ ID NO 24
<211> LENGTH: 23
<212> TYPE: RNA
<213> ORGANISM: Bacteriophage MS2

<400> SEQUENCE: 24
aauggauguc cauccucggu cag                                             23

<210> SEQ ID NO 25
<211> LENGTH: 22
<212> TYPE: RNA
<213> ORGANISM: Bacteriophage MS2

<400> SEQUENCE: 25
ggacuguaca uccucguagg gu                                              22

<210> SEQ ID NO 26
<211> LENGTH: 19
<212> TYPE: RNA
<213> ORGANISM: Bacteriophage MS2

<400> SEQUENCE: 26
agcucuuucc ucugaaaug                                                  19

<210> SEQ ID NO 27
<211> LENGTH: 18
<212> TYPE: RNA
<213> ORGANISM: Bacteriophage MS2

<400> SEQUENCE: 27
gaaaauccuc uggaacgu                                                   18
```

```
<210> SEQ ID NO 28
<211> LENGTH: 28
<212> TYPE: RNA
<213> ORGANISM: Bacteriophage MS2

<400> SEQUENCE: 28
ccaucggucu cuccuccaac gguuauuc                                          28

<210> SEQ ID NO 29
<211> LENGTH: 17
<212> TYPE: RNA
<213> ORGANISM: Bacteriophage MS2

<400> SEQUENCE: 29
uggacccucc ucucggc                                                      17

<210> SEQ ID NO 30
<211> LENGTH: 23
<212> TYPE: RNA
<213> ORGANISM: Bacteriophage MS2

<400> SEQUENCE: 30
gauggcuccu cucgagcgag cga                                               23

<210> SEQ ID NO 31
<211> LENGTH: 16
<212> TYPE: RNA
<213> ORGANISM: Bacteriophage MS2

<400> SEQUENCE: 31
cgagcugucc uucaac                                                       16

<210> SEQ ID NO 32
<211> LENGTH: 19
<212> TYPE: RNA
<213> ORGANISM: Bacteriophage MS2

<400> SEQUENCE: 32
ggaauccuua ccuuaaggc                                                    19

<210> SEQ ID NO 33
<211> LENGTH: 20
<212> TYPE: RNA
<213> ORGANISM: Bacteriophage MS2

<400> SEQUENCE: 33
gagaguaucc uucuuugaga                                                   20

<210> SEQ ID NO 34
<211> LENGTH: 24
<212> TYPE: RNA
<213> ORGANISM: Bacteriophage MS2

<400> SEQUENCE: 34
guacgccgau guccuucgag augu                                              24

<210> SEQ ID NO 35
<211> LENGTH: 12
<212> TYPE: RNA
<213> ORGANISM: Bacteriophage MS2

<400> SEQUENCE: 35
agcaucgcuu uu                                                           12
```

```
<210> SEQ ID NO 36
<211> LENGTH: 12
<212> TYPE: RNA
<213> ORGANISM: Bacteriophage MS2

<400> SEQUENCE: 36
ggaugucgcu au                                                             12

<210> SEQ ID NO 37
<211> LENGTH: 41
<212> TYPE: RNA
<213> ORGANISM: Bacteriophage MS2

<400> SEQUENCE: 37
agcagcguuc gcuugguaga ugcgacggga cgacucgguc u                             41

<210> SEQ ID NO 38
<211> LENGTH: 18
<212> TYPE: RNA
<213> ORGANISM: Bacteriophage MS2

<400> SEQUENCE: 38
cgaaucgcua ucgauucc                                                       18

<210> SEQ ID NO 39
<211> LENGTH: 19
<212> TYPE: RNA
<213> ORGANISM: Bacteriophage MS2

<400> SEQUENCE: 39
ggggcaaucg cuucaacga                                                      19

<210> SEQ ID NO 40
<211> LENGTH: 17
<212> TYPE: RNA
<213> ORGANISM: Bacteriophage MS2

<400> SEQUENCE: 40
uagguaaguc gcugggg                                                        17

<210> SEQ ID NO 41
<211> LENGTH: 27
<212> TYPE: RNA
<213> ORGANISM: Bacteriophage MS2

<400> SEQUENCE: 41
ccuuggugcg auacaucgcu ggugaca                                             27

<210> SEQ ID NO 42
<211> LENGTH: 34
<212> TYPE: RNA
<213> ORGANISM: Bacteriophage MS2

<400> SEQUENCE: 42
aacgcaagag cucgcuaugc ucguucugcc uuug                                     34

<210> SEQ ID NO 43
<211> LENGTH: 18
<212> TYPE: RNA
<213> ORGANISM: Bacteriophage MS2

<400> SEQUENCE: 43
aacaagucgc uugaagaa                                                       18
```

```
<210> SEQ ID NO 44
<211> LENGTH: 21
<212> TYPE: RNA
<213> ORGANISM: Bacteriophage MS2

<400> SEQUENCE: 44
ucgcuccagg cagguggcu u                                              21

<210> SEQ ID NO 45
<211> LENGTH: 20
<212> TYPE: RNA
<213> ORGANISM: Bacteriophage MS2

<400> SEQUENCE: 45
aggucaucgc ugucuucguu                                               20

<210> SEQ ID NO 46
<211> LENGTH: 10
<212> TYPE: RNA
<213> ORGANISM: Bacteriophage MS2

<400> SEQUENCE: 46
agcgcuccuu                                                          10

<210> SEQ ID NO 47
<211> LENGTH: 17
<212> TYPE: RNA
<213> ORGANISM: Bacteriophage MS2

<400> SEQUENCE: 47
augcccauag gcgcucg                                                  17

<210> SEQ ID NO 48
<211> LENGTH: 25
<212> TYPE: RNA
<213> ORGANISM: Bacteriophage MS2

<400> SEQUENCE: 48
uugguauagu gcuaugcagc gcuau                                         25

<210> SEQ ID NO 49
<211> LENGTH: 21
<212> TYPE: RNA
<213> ORGANISM: Bacteriophage MS2

<400> SEQUENCE: 49
uagccaucgg ucucuccucc a                                             21

<210> SEQ ID NO 50
<211> LENGTH: 25
<212> TYPE: RNA
<213> ORGANISM: Bacteriophage MS2

<400> SEQUENCE: 50
gauguccauc cucggucagc uguug                                         25

<210> SEQ ID NO 51
<211> LENGTH: 11
<212> TYPE: RNA
<213> ORGANISM: Bacteriophage MS2

<400> SEQUENCE: 51
aaucgagcug u                                                        11
```

-continued

```
<210> SEQ ID NO 52
<211> LENGTH: 11
<212> TYPE: RNA
<213> ORGANISM: Bacteriophage MS2

<400> SEQUENCE: 52
ccucgagcga c                                                          11

<210> SEQ ID NO 53
<211> LENGTH: 20
<212> TYPE: DNA
<213> ORGANISM: Artificial Sequence
<220> FEATURE:
<223> OTHER INFORMATION: Primer B3 from Table 1

<400> SEQUENCE: 53
agcacaccca ccccgtttac                                                 20

<210> SEQ ID NO 54
<211> LENGTH: 20
<212> TYPE: DNA
<213> ORGANISM: Artificial Sequence
<220> FEATURE:
<223> OTHER INFORMATION: Primer B4 from Table 1

<400> SEQUENCE: 54
ggtccgtccc accgaagaac                                                 20

<210> SEQ ID NO 55
<211> LENGTH: 20
<212> TYPE: DNA
<213> ORGANISM: Artificial Sequence
<220> FEATURE:
<223> OTHER INFORMATION: Primer B5 from Table 1

<400> SEQUENCE: 55
agaacttgcg ttctcgagcg                                                 20

<210> SEQ ID NO 56
<211> LENGTH: 20
<212> TYPE: DNA
<213> ORGANISM: Artificial Sequence
<220> FEATURE:
<223> OTHER INFORMATION: Primer B7 from Table 1

<400> SEQUENCE: 56
tataacgcgc acgccggcgg                                                 20

<210> SEQ ID NO 57
<211> LENGTH: 20
<212> TYPE: DNA
<213> ORGANISM: Artificial Sequence
<220> FEATURE:
<223> OTHER INFORMATION: Primer B8 from Table 1

<400> SEQUENCE: 57
cggagtcttg gtgtataccg                                                 20

<210> SEQ ID NO 58
<211> LENGTH: 20
<212> TYPE: DNA
<213> ORGANISM: Artificial Sequence
<220> FEATURE:
<223> OTHER INFORMATION: Primer C2 from Table 1
```

<400> SEQUENCE: 58
gcggatacga tcgagatatg                                               20

<210> SEQ ID NO 59
<211> LENGTH: 20
<212> TYPE: DNA
<213> ORGANISM: Artificial Sequence
<220> FEATURE:
<223> OTHER INFORMATION: Primer C3 from Table 1

<400> SEQUENCE: 59
gcgcacattg gtctcggacc                                               20

<210> SEQ ID NO 60
<211> LENGTH: 20
<212> TYPE: DNA
<213> ORGANISM: Artificial Sequence
<220> FEATURE:
<223> OTHER INFORMATION: Primer D from Table 1

<400> SEQUENCE: 60
ccgctctcag agcgcggggg                                               20

<210> SEQ ID NO 61
<211> LENGTH: 20
<212> TYPE: DNA
<213> ORGANISM: Artificial Sequence
<220> FEATURE:
<223> OTHER INFORMATION: Primer D1 from Table 1

<400> SEQUENCE: 61
gcaattgatt ggtaaatttc                                               20

<210> SEQ ID NO 62
<211> LENGTH: 20
<212> TYPE: DNA
<213> ORGANISM: Artificial Sequence
<220> FEATURE:
<223> OTHER INFORMATION: Primer D2 from Table 1

<400> SEQUENCE: 62
tctctattta tctgaccgcg                                               20

<210> SEQ ID NO 63
<211> LENGTH: 20
<212> TYPE: DNA
<213> ORGANISM: Artificial Sequence
<220> FEATURE:
<223> OTHER INFORMATION: Primer D5 from Table 1

<400> SEQUENCE: 63
aattcgtccc ttaagtaagc                                               20

<210> SEQ ID NO 64
<211> LENGTH: 20
<212> TYPE: DNA
<213> ORGANISM: Artificial Sequence
<220> FEATURE:
<223> OTHER INFORMATION: Primer E from Table 1

<400> SEQUENCE: 64
gaagatcaat acataaagag                                               20

```
<210> SEQ ID NO 65
<211> LENGTH: 20
<212> TYPE: DNA
<213> ORGANISM: Artificial Sequence
<220> FEATURE:
<223> OTHER INFORMATION: Primer E1 from Table 1

<400> SEQUENCE: 65
tgcattgcct taacaataag                                          20

<210> SEQ ID NO 66
<211> LENGTH: 20
<212> TYPE: DNA
<213> ORGANISM: Artificial Sequence
<220> FEATURE:
<223> OTHER INFORMATION: Primer E2 from Table 1

<400> SEQUENCE: 66
tacaggttac tttgtaagcc                                          20

<210> SEQ ID NO 67
<211> LENGTH: 20
<212> TYPE: DNA
<213> ORGANISM: Artificial Sequence
<220> FEATURE:
<223> OTHER INFORMATION: Primer G from Table 1

<400> SEQUENCE: 67
gagccgttgc ctgattaatg                                          20

<210> SEQ ID NO 68
<211> LENGTH: 20
<212> TYPE: DNA
<213> ORGANISM: Artificial Sequence
<220> FEATURE:
<223> OTHER INFORMATION: Primer H from Table 1

<400> SEQUENCE: 68
agcgtcaacg cttatgatgg                                          20

<210> SEQ ID NO 69
<211> LENGTH: 18
<212> TYPE: DNA
<213> ORGANISM: Artificial Sequence
<220> FEATURE:
<223> OTHER INFORMATION: Primer I from Table 1

<400> SEQUENCE: 69
agcatcccac gggggccg                                            18

<210> SEQ ID NO 70
<211> LENGTH: 20
<212> TYPE: DNA
<213> ORGANISM: Artificial Sequence
<220> FEATURE:
<223> OTHER INFORMATION: Primer J from Table 1

<400> SEQUENCE: 70
ggttcaagat acctagagac                                          20

<210> SEQ ID NO 71
<211> LENGTH: 20
<212> TYPE: DNA
<213> ORGANISM: Artificial Sequence
<220> FEATURE:
<223> OTHER INFORMATION: Primer J1 from Table 1
```

```
<400> SEQUENCE: 71
gacggccatc taacttgatg                                                   20

<210> SEQ ID NO 72
<211> LENGTH: 20
<212> TYPE: DNA
<213> ORGANISM: Artificial Sequence
<220> FEATURE:
<223> OTHER INFORMATION: Primer K1 from Table 1

<400> SEQUENCE: 72
cttcggtcga cgcccggttc                                                   20

<210> SEQ ID NO 73
<211> LENGTH: 20
<212> TYPE: DNA
<213> ORGANISM: Artificial Sequence
<220> FEATURE:
<223> OTHER INFORMATION: Primer L1 from Table 1

<400> SEQUENCE: 73
tagccatggt agcgtctcgc                                                   20

<210> SEQ ID NO 74
<211> LENGTH: 20
<212> TYPE: DNA
<213> ORGANISM: Artificial Sequence
<220> FEATURE:
<223> OTHER INFORMATION: Primer L2 from Table 1

<400> SEQUENCE: 74
cctatcaagg gtactaaaag                                                   20

<210> SEQ ID NO 75
<211> LENGTH: 11
<212> TYPE: RNA
<213> ORGANISM: Bacteriophage MS2

<400> SEQUENCE: 75
acgcuccugc u                                                            11

<210> SEQ ID NO 76
<211> LENGTH: 11
<212> TYPE: RNA
<213> ORGANISM: Bacteriophage MS2

<400> SEQUENCE: 76
uggcuccuac c                                                            11

<210> SEQ ID NO 77
<211> LENGTH: 11
<212> TYPE: RNA
<213> ORGANISM: Bacteriophage MS2

<400> SEQUENCE: 77
augcuccuac a                                                            11

<210> SEQ ID NO 78
<211> LENGTH: 11
<212> TYPE: RNA
<213> ORGANISM: Bacteriophage MS2

<400> SEQUENCE: 78
agucuccuuu c                                                            11
```

```
<210> SEQ ID NO 79
<211> LENGTH: 11
<212> TYPE: RNA
<213> ORGANISM: Bacteriophage MS2

<400> SEQUENCE: 79
ggucuccuaa a                                                          11

<210> SEQ ID NO 80
<211> LENGTH: 11
<212> TYPE: RNA
<213> ORGANISM: Bacteriophage MS2

<400> SEQUENCE: 80
aaccuccucu c                                                          11

<210> SEQ ID NO 81
<211> LENGTH: 11
<212> TYPE: RNA
<213> ORGANISM: Bacteriophage MS2

<400> SEQUENCE: 81
gcucuccucc c                                                          11

<210> SEQ ID NO 82
<211> LENGTH: 11
<212> TYPE: RNA
<213> ORGANISM: Bacteriophage MS2

<400> SEQUENCE: 82
gcucuccucg g                                                          11

<210> SEQ ID NO 83
<211> LENGTH: 11
<212> TYPE: RNA
<213> ORGANISM: Bacteriophage MS2

<400> SEQUENCE: 83
aacuuccugu c                                                          11

<210> SEQ ID NO 84
<211> LENGTH: 11
<212> TYPE: RNA
<213> ORGANISM: Bacteriophage MS2

<400> SEQUENCE: 84
ccauuccuag g                                                          11

<210> SEQ ID NO 85
<211> LENGTH: 11
<212> TYPE: RNA
<213> ORGANISM: Bacteriophage MS2

<400> SEQUENCE: 85
uucuuccuau g                                                          11

<210> SEQ ID NO 86
<211> LENGTH: 11
<212> TYPE: RNA
<213> ORGANISM: Bacteriophage MS2

<400> SEQUENCE: 86
agcuuccugu a                                                          11
```

```
<210> SEQ ID NO 87
<211> LENGTH: 11
<212> TYPE: RNA
<213> ORGANISM: Bacteriophage MS2

<400> SEQUENCE: 87
aucuuccucg c                                                          11

<210> SEQ ID NO 88
<211> LENGTH: 15
<212> TYPE: RNA
<213> ORGANISM: Bacteriophage MS2

<400> SEQUENCE: 88
aauuuucgcu acgaa                                                      15

<210> SEQ ID NO 89
<211> LENGTH: 15
<212> TYPE: RNA
<213> ORGANISM: Bacteriophage MS2

<400> SEQUENCE: 89
ggcuaucgcu guagg                                                      15

<210> SEQ ID NO 90
<211> LENGTH: 15
<212> TYPE: RNA
<213> ORGANISM: Bacteriophage MS2

<400> SEQUENCE: 90
augguucgcu ugcga                                                      15

<210> SEQ ID NO 91
<211> LENGTH: 15
<212> TYPE: RNA
<213> ORGANISM: Bacteriophage MS2

<400> SEQUENCE: 91
agcuaucgcu aagcu                                                      15

<210> SEQ ID NO 92
<211> LENGTH: 15
<212> TYPE: RNA
<213> ORGANISM: Bacteriophage MS2

<400> SEQUENCE: 92
caacuucgcu aacgg                                                      15

<210> SEQ ID NO 93
<211> LENGTH: 15
<212> TYPE: RNA
<213> ORGANISM: Bacteriophage MS2

<400> SEQUENCE: 93
cggggucgcu gaaug                                                      15

<210> SEQ ID NO 94
<211> LENGTH: 15
<212> TYPE: RNA
<213> ORGANISM: Bacteriophage MS2

<400> SEQUENCE: 94
aguggucgcu acaua                                                      15
```

```
<210> SEQ ID NO 95
<211> LENGTH: 15
<212> TYPE: RNA
<213> ORGANISM: Bacteriophage MS2

<400> SEQUENCE: 95
ucguaucgcu cgaga                                                          15

<210> SEQ ID NO 96
<211> LENGTH: 15
<212> TYPE: RNA
<213> ORGANISM: Bacteriophage MS2

<400> SEQUENCE: 96 uucgucgcu acugg                                                           15

<210> SEQ ID NO 97
<211> LENGTH: 15
<212> TYPE: RNA
<213> ORGANISM: Bacteriophage MS2

<400> SEQUENCE: 97
gaaguucgcu gaaca                                                          15

<210> SEQ ID NO 98
<211> LENGTH: 15
<212> TYPE: RNA
<213> ORGANISM: Bacteriophage MS2

<400> SEQUENCE: 98
ggaccucgcu gccga                                                          15

<210> SEQ ID NO 99
<211> LENGTH: 15
<212> TYPE: RNA
<213> ORGANISM: Bacteriophage MS2

<400> SEQUENCE: 99
cuuccucgcg aucuu                                                          15

<210> SEQ ID NO 100
<211> LENGTH: 15
<212> TYPE: RNA
<213> ORGANISM: Bacteriophage MS2

<400> SEQUENCE: 100
gcugcucgcg gauac                                                          15

<210> SEQ ID NO 101
<211> LENGTH: 15
<212> TYPE: RNA
<213> ORGANISM: Bacteriophage MS2

<400> SEQUENCE: 101
acauaucgcg acgua                                                          15

<210> SEQ ID NO 102
<211> LENGTH: 15
<212> TYPE: RNA
<213> ORGANISM: Bacteriophage MS2

<400> SEQUENCE: 102
cucucuggcu accga                                                          15
```

-continued

```
<210> SEQ ID NO 103
<211> LENGTH: 15
<212> TYPE: RNA
<213> ORGANISM: Bacteriophage MS2

<400> SEQUENCE: 103
ucgacuggcu ccuac                                                    15

<210> SEQ ID NO 104
<211> LENGTH: 15
<212> TYPE: RNA
<213> ORGANISM: Bacteriophage MS2

<400> SEQUENCE: 104
gcgucuggcu cagca                                                    15

<210> SEQ ID NO 105
<211> LENGTH: 15
<212> TYPE: RNA
<213> ORGANISM: Bacteriophage MS2

<400> SEQUENCE: 105
uaccuuagcu aucgc                                                    15

<210> SEQ ID NO 106
<211> LENGTH: 15
<212> TYPE: RNA
<213> ORGANISM: Bacteriophage MS2

<400> SEQUENCE: 106
ccgucuugcu cguau                                                    15

<210> SEQ ID NO 107
<211> LENGTH: 15
<212> TYPE: RNA
<213> ORGANISM: Bacteriophage MS2

<400> SEQUENCE: 107
acguaucgug auaug                                                    15

<210> SEQ ID NO 108
<211> LENGTH: 15
<212> TYPE: RNA
<213> ORGANISM: Bacteriophage MS2

<400> SEQUENCE: 108
cugucgagcu aaugc                                                    15

<210> SEQ ID NO 109
<211> LENGTH: 15
<212> TYPE: RNA
<213> ORGANISM: Bacteriophage MS2

<400> SEQUENCE: 109
ccagcgagcu cuccu                                                    15

<210> SEQ ID NO 110
<211> LENGTH: 15
<212> TYPE: RNA
<213> ORGANISM: Bacteriophage MS2

<400> SEQUENCE: 110
cuacauagcg ugguu                                                    15
```

COLD SHOCK PROTEIN COMPOSITIONS AND METHODS AND KITS FOR THE USE THEREOF

CLAIM OF PRIORITY

This application claims priority to U.S. Provisional Application No. 61/067,596, filed Feb. 29, 2008, U.S. Provisional Application No. 61/195,747, filed Oct. 9, 2008, and Japanese Application No. 2008-129745, filed May 16, 2008, the disclosures of which are hereby incorporated by reference in their entireties.

SEQUENCE LISTINGS

Sequence listings in written and computer readable form are submitted herewith. The information recorded in computer readable form is identical to the written sequence listings.

BACKGROUND OF THE INVENTION

The synthesis of DNA is used for various purposes in the research field. Among them, much of the DNA syntheses are carried out by the enzymatic methods utilizing DNA polymerase, except for chemical synthesis of a short strand DNA such as an oligonucleotide. PCR, which can easily amplify the desired nucleic acid fragments in vitro, is highly valuable, and has become an indispensable tool in biology, medicine, agriculture, and other fields. In the amplification of DNA by PCR, high specificity of reaction is required in many cases. Despite developments of new DNA polymerase, and optimization of the composition of reaction mixture to reduce the non-specific amplification, there is still a need for improvements in PCR amplification specificity.

In addition to traditional PCR methods, which use DNA as the template material, DNA synthesis may also be achieved by utilizing the RNA-dependent DNA polymerase reverse transcriptase. In the research field, it is often necessary to analyze mRNA molecules derived from various genes. Reverse transcriptase enables the reverse transcription reaction for synthesizing cDNA using RNA as a template and, as a result, remarkable advancements have been achieved in the analysis of the mRNA molecules. The analysis of the mRNA molecules, in which the reverse transcriptase is used, is now an indispensable experimental technique in genetic studies, and has become an absolutely necessary technique in the various fields such as biology, medicine, and agriculture by applying in the cloning techniques and PCR techniques.

Some approaches have been so far made in order to improve the reactivity of the reverse transcription reaction. It has been studied, for example, a process of reverse transcription reaction which is performed at high temperatures; a cDNA synthesis process wherein a reverse transcriptase and an enzyme having the 3'-5' exonuclease activity are used (JP Patent No. 3910015); a process wherein nucleic acid-binding proteins such as Ncp7, recA, SSB and T4gp32 are utilized (WO 00/55307); and the like. Despite the improvements that have been made in the reactivity of the reverse transcription reaction, cDNA of full-length may not be synthesized, and an amount of the synthesized cDNA may not be enough in some cases even today. Therefore, the improvement of the reactivity of the reverse transcription reaction is still an ongoing issue to be desirably further improved.

In addition to improvements to the two DNA synthesis methods described above, there is also a need in the scientific field for a technique by which to determine endoribonuclease cleavage-site specificity. mRNA interferases, for example, are sequence-specific endoribonucleases encoded by the toxin-antitoxin systems that are present in a wide range of bacterial genomes. These endoribonucleases usually have specific cleavage sites within single-strand RNA: E. coli MazF specifically cleaves at ACA sequences, ChpBK at ACY sequences (Y is U, A, or G), PemK from plasmid R100 at UAH sequences (where H is C, A, or U), and MazF-mt1 and MazF-mt6 from M. tuberculosis at UAC and U rich regions, respectively. It was recently found that a MazF homolog from Staphylococcus aureus cleaves at VUUV' (where V and V' are A, C, or G and may or may not be identical). However previous attempts to determine the cleavage specificities of some of the MazF homologs of M. tuberculosis have failed. Particularly for the determination of the cleavage specificity where a specific sequence longer than three bases is recognized, it is essential to use an RNA substrate that is long enough to cover all possible target sequences. A major problem in using long RNA as a substrate, however, is that although it is a single-stranded RNA, it forms extensive stable secondary structures. In order to use this or any other long RNA as a substrate for endoribonucleases, its secondary structures have to be unfolded. Thus there remains a need to develop new techniques to determine cleavage-site specificity for endoribonucleases such as mRNA interferases.

Cold shock proteins are found in various microorganisms, and are deemed to play some roles in the adaptation to the downshift of the growth temperature. Among them, CspA has been identified as a major cold shock protein. The gene encoding CspA was isolated from Escherichia coli, and a recombinant CspA was produced using its gene (see WO 90/09444). However, the conventionally proposed applications of cold shock proteins have been limited to their use as a cryoprotective protein which prevents freezing or frost damage in agricultural fields.

The present invention provides cold shock protein-containing compositions for improved DNA synthesis reactions with improved reactivity, methods for synthesizing DNA using such compositions, kits for use in such methods, and synthetic DNA products yielded by such methods. The present invention further provides cold shock protein-containing compositions for the identification of endoribonuclease cleavage sites, methods for identifying endoribonuclease cleavage sites using such compositions, and kits for use in such methods.

SUMMARY OF THE INVENTION

According to the present invention, a composition useful for DNA synthesis using DNA polymerase, a method for synthesizing DNA using such composition, a kit for use in such method for the DNA synthesis, and a DNA composition synthesized according to such method are provided. It is an object of the present invention to enable DNA synthesis using DNA polymerase in which the reactivity of the reaction is improved.

An embodiment of the present invention relates to a composition for DNA synthesis comprising a cold shock protein and a DNA polymerase. In certain embodiments of the present invention, it is exemplified by CspA or a homolog thereof, preferably, CspA derived from Escherichia coli or a homolog thereof as the cold shock protein. The composition may comprise more than 0.5 µg of CspA per 25

µL of the composition. The composition according to such an embodiment may comprise two or more kinds of DNA polymerases. Further, the composition according to such embodiment may comprise at least one primer and at least one deoxyribonucleotide. Such composition may further comprise a liquid vehicle, such as a reaction buffer solution.

A further embodiment of the present invention comprises A) a cold shock protein; B) at least one component selected from the group consisting of DNA polymerase, a primer, a deoxyribonucleotide, and DNA; and C) a liquid vehicle.

A further embodiment of the present invention relates to a method for synthesizing DNA, which comprises the steps of A) preparing a mixture comprising a cold shock protein, a DNA polymerase, at least one primer, at least one deoxyribonucleotide triphosphate, and DNA; and B) incubating the mixture prepared in step A).

Another embodiment of the present invention relates to a kit for DNA synthesis comprising a cold shock protein and a DNA polymerase. The kit according so such an embodiment may further comprise a liquid vehicle or instructions in paper or electronic form for utilizing the kit. The components of such kit may be present individually or separately. The present invention also relates to a DNA composition synthesized by a process comprising the steps of: A) preparing a mixture comprising a cold shock protein, a DNA polymerase, at least one primer, at least one deoxyribonucleotide, and DNA; and B) incubating the mixture prepared in step A).

The present invention also relates to a composition advantageously used for the reverse transcription reaction, a cDNA synthesis process using said composition, a kit advantageously used for the reverse transcription reaction, and a cDNA composition synthesized by such process. According to the present invention, such a favorable reverse transcription reaction that is superior in its reactivity in view of specificity, length of the strand synthesized, an amount of the synthesis and the like, can be realized.

An embodiment of the present invention relates to a composition for reverse transcription reaction comprising a cold shock protein or a homolog thereof; and a reverse transcriptase. In such an embodiment according to the present invention, an example of the cold shock protein is CspA or a homolog thereof, and an example of the CspA is CspA derived from *Escherichia coli*. In some embodiments, the CspA may be present in a quantity of from about 0.5 µg to about 20 µg of CspA per 20 µL of the composition. Examples of the reverse transcriptase are a reverse transcriptase derived from Moloney Murine Leukemia Virus and/or a reverse transcriptase derived from Avian Myeloblastosis Virus and/or combinations thereof. Further, the composition in this embodiment according to the present invention may further include at least one primer and at least one deoxyribonucleotide. Further embodiments of the composition comprise a liquid vehicle, such as a reaction buffer solution. Other embodiments comprise an oligo (dT) primer or an oligonucleotide primer having a random sequence or a combination thereof.

A further embodiment of the present invention comprises a composition for reverse transcription reaction comprising: A) a cold shock protein; B) at least one component selected from the group consisting of reverse transcriptase, a primer, a deoxyribonucleotide, and RNA; and C) a liquid vehicle.

A further embodiment of the present invention relates to a process for synthesizing cDNA, comprising: A) preparing a mixture comprising a cold shock protein, a reverse transcriptase, at least one primer, at least one deoxyribonucleotide, and RNA; and B) incubating the mixture prepared in the step A).

A further embodiment of the present invention relates to a kit for reverse transcription reaction comprising: A) a cold shock protein; B) at least one component selected from the group consisting of reverse transcriptase, a primer, a deoxyribonucleotide, and RNA; and C) a liquid vehicle. The kit according so such an embodiment may further comprise a liquid vehicle or instructions in paper or electronic form for utilizing the kit. The components of such kit may be present individually or separately. The kit of such an embodiment may further comprise a reagent for performing a gene amplification reaction.

The present invention further relates to a cDNA composition synthesized by a process comprising the steps of: A) preparing a solution comprising a cold shock protein, a reverse transcriptase, at least one primer, at least one deoxyribonucleotide, and RNA; and B) incubating the solution prepared in the step A).

The present invention further relates to a composition for identifying endoribonuclease cleavage sites, methods for identifying endoribonuclease cleavage sites using such compositions, and kits for use in such methods.

An embodiment of the present invention relates to a composition for identifying endoribonuclease cleavage sites A) a cold shock protein; and B) at least one component selected from the group consisting of an RNA substrate and an endoribonuclease. In such an embodiment according to the present invention, an example of the cold shock protein is CspA or a homolog thereof, and an example of the CspA is CspA derived from *Escherichia coli*. In preferred embodiments, the RNA substrate is longer than 1024 bases and contains approximately an equal number of each base. An example of such an RNA substrate is bacteriophage MS2 RNA. The composition of such an embodiment may further comprise a liquid vehicle.

Another embodiment of the present invention relates to a method for determining endoribonuclease cleavage sites, which comprises the steps of: A) preparing a mixture comprising a cold shock protein, an RNA substrate, and an endoribonuclease; and B) incubating the mixture in step A). Such method may further comprise analyzing the mixture by electrophoresis.

A further embodiment of the present invention relates to a kit for determining endoribonuclease cleavage sites comprising a cold shock protein and an RNA substrate. The kit of such embodiment may further comprise a liquid vehicle, such as a reaction buffer solution. Such embodiment may further comprise instructions in paper or electronic form for utilizing such kit. In such embodiment, the cold shock protein and RNA substrate may be present individually or combined.

As used herein, cold shock protein is a collective designation for proteins which are expressed in organisms, particularly in microorganisms, when they are exposed to the cold shock by downshift of growth temperatures. When an incubation temperature of *Escherichia coli* is reduced from 37° C. to 15° C., cold shock protein, which is called CspA, is transiently expressed at a high level. It is known that *Escherichia coli* has eight different proteins, CspB to CspI, which have high amino acid sequence identity to CspA. Of these proteins, CspB, CspG and CspI are the cold shock proteins. Further, it is conventionally known that homologs of these cold shock proteins exist in other microorganisms such as *Bacillus subtilis* (CspB), *Bacillus caldolyticus* (CspB), *Thermotoga maritima* (CspB, CspL) and *Lactoba-*

*cillus plantarum* (CspL). In the present invention, the homolog of the CspA refers to cold shock protein having an amino acid sequence showing at least 50% sequence identity with the amino acid sequence of CspA derived from *Escherichia coli*. In the present invention, these cold shock proteins can be used. An example of cold shock protein used in the present invention is preferably CspA, more preferably CspA derived from Gram-negative bacteria, and even more preferably CspA derived from *Escherichia coli*. The CspA used in the present invention may be prepared by recombinant DNA technology or may be isolated from a microorganism.

Homolog means an entity having sequence homology with a subject protein, preferably showing at least 50% sequence identity with the amino acid sequence of another polypeptide, and having similarity in structural characteristics or biological function.

As used herein, deoxyribonucleotide refers to phosphate groups bonded to deoxyribose bonded to organic bases by the phosphoester bond. A natural DNA includes four different nucleotides. The nucleotides respectively consisting of adenine, guanine, cytosine and thymine bases can be found in the natural DNA. The, adenine, guanine, cytosine and thymine bases, are respectively abbreviated as A, G, C and T. The deoxyribonucleotide includes free monophosphate, diphosphate and triphosphate (more specifically, the phosphate groups each includes one, two or three phosphate portions). Therefore, the deoxyribonucleotide includes deoxyribonucleotide triphosphate (for example, dATP, dCTP, dITP, dGTP and dTTP) and derivatives thereof. The deoxyribonucleotide derivative includes [αS]dATP, 7-deaza-dGTP, 7-deaza-dATP and a deoxynucleotide derivative showing resistance against the decomposition of nucleic acid. The nucleotide derivative includes, for example, deoxyribonucleotide labeled in such a manner that can be detected by a radioactive isotope such as $^{32}P$ or $^{35}S$, a fluorescent portion, a chemiluminescent portion, a bioluminescent portion or an enzyme.

As used herein, deoxyribonucleotide triphosphate refers to a nucleotide of which the sugar portion is composed of deoxyribose, and having triphosphate group. A natural DNA includes four different nucleotides which respectively has adenine, guanine, cytosine and thymine as the base portion. The deoxyribonucleotide triphosphate contained in the compositions of the present invention is a mixture of four deoxyribonucleotides triphosphate, dATP, dCTP, dGTP, and dTTP. In the present invention, the derivatives of the deoxyribonucleotide triphosphate can be also used. The deoxyribonucleotide triphosphate derivative includes [αS]dATP, 7-deaza-dGTP, 7-deaza-dATP and a deoxynucleotide derivative showing resistance against the digestion of nucleic acid. The nucleotide derivative also includes, for example, deoxyribonucleotide triphosphate labeled in such a manner that can be detected by a radioactive isotope such as $^{32}P$ or $^{35}S$, a fluorescent molecule, a chemiluminescent molecule, a bioluminescent molecule or an enzyme.

As used herein, the reaction buffer solution means a solution including a buffer agent or a buffer agent mixture, and may further include divalent cations and monovalent cations.

To the extent the term "or" is used herein (e.g. A or B), it is intended to mean "A or B or both." As used herein, use of the terms "a" or "an" or "the" are not intended to be limiting in quantity. For example, reference in the detailed description to "a cold shock protein" is not intended to mean "a single cold shock protein" and such reference may encompass either a single cold shock protein or multiple cold shock proteins.

BRIEF DESCRIPTION OF THE DRAWINGS

FIG. 14 depicts the secondary structure of MS2 RNA and enhancement of MazF-mt3 endoribonucleases activity of CspA. FIG. 14B depicts enhancement of endoribonuclease activity by RNA chaperone CspA. The full-length MS2 mRNAs were partially digested at 37° C. with (lanes 3, 4, 5 and 6) or without (lanes 1 and 2) purified N-terminal His-tagged MazF-mt3, with (lanes 2 and 5, 32 µg; lane 4, 16

Figure 1:
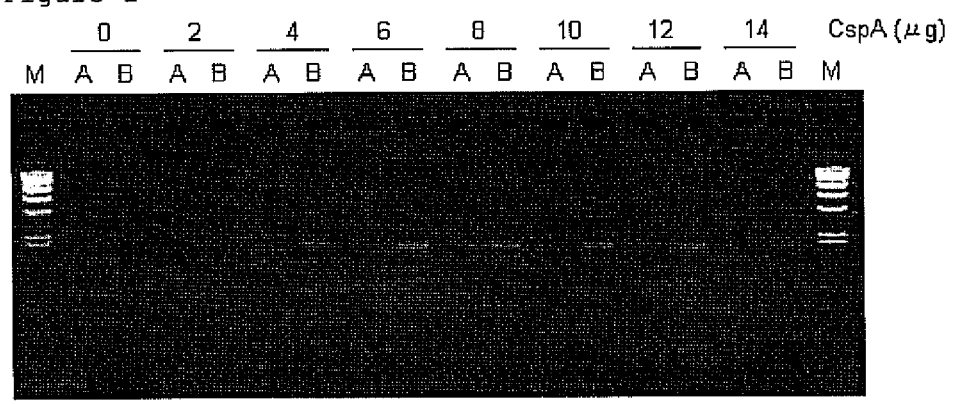
FIG. 1 illustrates the result of agarose gel electrophoresis of DNA fragment amplified by Taq DNA polymerase in the presence or in the absence of CspA. HindIII-digested lambda DNAs are electrophoresed in the lanes marked with "M".

μg; lane 6, 64 μg) or without (lanes 1 and 3) purified CspA protein. The digestion reaction mixture (10 μl) consisted of 1.6 μg of MS2 RNA substrate, 1.6 μg of MazF-mt3(His)$_6$, 16, 32 or 64 μg CspA and 0.5 μl of RNase inhibitor (Roche) in 10 mM Tris-HCl (pH 7.8). The reaction products were run on a 1.2% (1×TBE) agarose gel.

FIGS. 15 A-H depict in vitro cleavage of the MS2 RNA with (His)$_6$MazF-mt3, demonstrating that MazF-mt3 cleaves specifically at UUCCU sites. Lane 1 represents control reaction in which no proteins were added; lane 2, a control reaction in which only CspA protein was added; lane 3, MS2 RNA only with (His)$_6$MazF-mt3; lane 4, MS2 RNA incubated with (His)$_6$MazF-mt3 and CspA protein. Cleavage sites are indicated by arrows on the RNA sequence and were determined using the RNA ladder shown on the right. In FIG. 15H the RNA ladder was compressed between the C (base 3390) and G (base 3394) residues, but the sequence was elucidated though comparison of the upstream and downstream regions with the standard sequence.

Figure 16B:
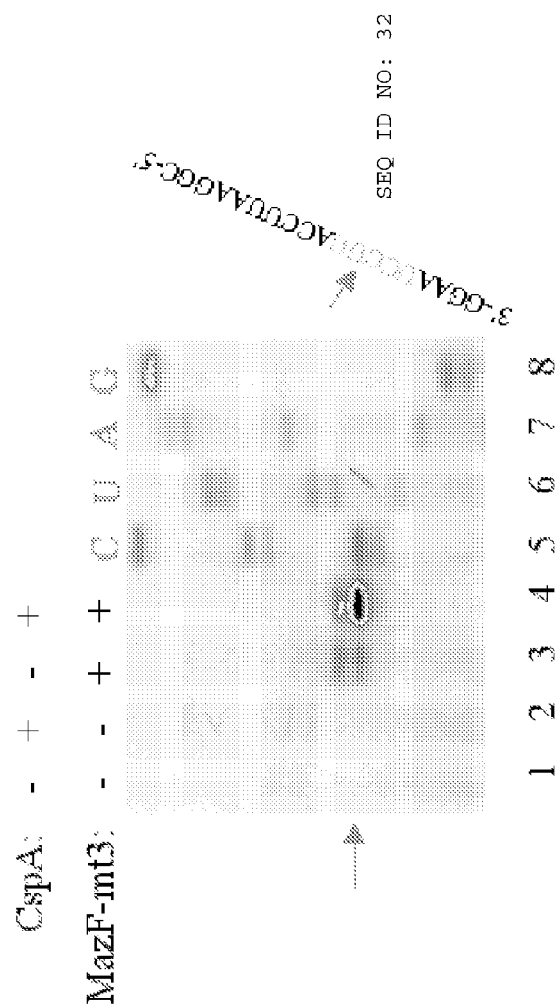
Figure 16D:
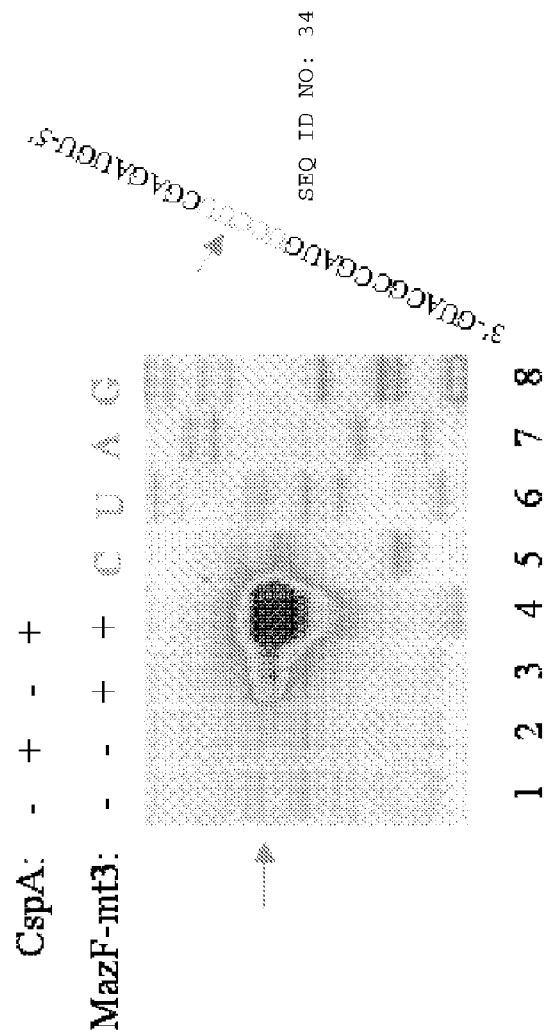

FIGS. 16 A-D depict in vitro cleavage of the MS2 RNA with (His)$_6$MizF-mt3, demonstrating that MazF-mt3 cleaves specifically at CUCCU sites. Lane 1, control reaction in which no proteins were added; lane 2, control reaction in which only CspA protein was added; lane 3, MS2 RNA incubated only with (His)$_6$MazF-mt3; lane 4, MS2 RNA incubated with (His)$_6$MazF-mt3 and CspA protein. Strong and weak cleavage sites are indicated by the arrows on the RNA sequence and were determined using the RNA ladder shown on the right.

FIGS. 17 A-R depict in vitro cleavage of the MS2 RNA with (His)$_6$MazF-mt7. Lane 1, control reaction in which no enzymes were added; lane 2, control reaction in which only CspA protein was added; lane 3, MS2 RNA incubated only with (His)$_6$MazF-mt3; lane 4, MS2 RNA incubated with (His)$_6$MazF-mt3 and CspA protein. Strong and weak cleavage sites are indicated by the arrows on the RNA sequence and were determined using the RNA ladder shown on the right.

DETAILED DESCRIPTION OF THE INVENTION

(1) Composition for Improved DNA Synthesis Using DNA Polymerase According to the Present Invention A composition of the present invention comprises a cold shock protein or a homolog thereof and a DNA polymerase. Surprisingly, the reactivity of a DNA synthesis reaction was improved in the case where a reaction mixture comprising cold shock protein and DNA polymerase were used in comparison to a DNA synthesis reaction in the absence of cold shock protein.

In the present invention, the above improvement of the reactivity of DNA synthesis means, although there are no particular limitations, a reduction of the non-specific amplification, an increase in the amount of the amplified products derived from the target sequence, and the like. Such improvement can be quantified by analyzing the product synthesized in the reaction mixture with conventional method, such as electrophoresis on agarose gel.

According to the DNA synthesis method of the present invention, the non-specific synthesis of DNA is repressed. Conventionally, there has been known that the reaction mixture for DNA synthesis should be kept at low temperature until start of the reaction to prevent the occurrence of non-specific reaction. The use of the composition according to the present invention enables DNA synthesis reaction using the mixtures standing at room temperature directly.

DNA polymerase which can be used for the present invention is not particularly limited; however, thermostable DNA polymerase is preferred. As the DNA polymerase available for the present invention, it is exemplified by DNA polymerase derived from the eubacteria such as bacterium belonging genus *Thermus* or *Bacillus* (DNA polymerase derived from *Thermus aquaticus, Bacillus caldotenax* and the like), DNA polymerase derived from the archaebacteria such as those belonging genus *Pyrococcus* or *Thermococcus* (DNA polymerase derived from *Pyrococcus furiosus, Thermococcus litralis, Thermococcus kodakaraensis* and the like). In DNA synthesis method of the present invention, the thermostable DNA polymerase which can be used in PCR is preferred.

Two or more kinds of DNA polymerases can be comprised in the composition of the present invention. For instance, combination of a DNA polymerase possessing 3'→5' exonuclease activity and another DNA polymerase possessing substantially no 3'→5' exonuclease activity can be used in the present invention. The technology using such combination of DNA polymerases is known as LA-PCR (Long and accurate PCR).

The composition according to the present invention may further comprise at least one primer, at least one deoxyribonucleotide triphosphate, and/or a reaction buffer solution in addition to the cold shock protein and the DNA polymerase.

The primer is oligonucleotide having a nucleotide sequence complementary to the template DNA. There is no specific limitation concerning the primer as long as it is capable of annealing to the template DNA under the reaction conditions used in the present invention.

A length of the primer is preferably at least six nucleotides since a specific annealing process is performed, and more preferably at least 10 nucleotides. The length of the primer is preferably at most 100 nucleotides and more preferably at most 30 nucleotides in terms of the synthesis of oligonucleotide. The oligonucleotide can be chemically synthesized by known method. The oligonucleotide may be oligonucleotide derived from natural source, and for example, may be prepared by digestion of DNA prepared from natural source with the restriction endonuclease.

The composition of the present invention is useful for the preparation of the mixture for DNA synthesis by DNA polymerase. A composition for DNA synthesis reaction including the cold shock protein or an accelerator for DNA synthesis reaction including the cold shock protein are also embodiments of the present invention.

(2) Method for Improved DNA Synthesis Using DNA Polymerase According to the Present Invention A method for synthesizing DNA of the present invention comprises the steps of:
A) preparing a mixture comprising a cold shock protein or a homolog thereof, a DNA polymerase, at least one primer, at least one deoxyribonucleotide triphosphate, and DNA as a template; and
B) incubating the mixture prepared in step A).

By the method of present invention, the reactivity of a DNA synthesis reaction was improved in comparison to a DNA synthesis reaction in the absence of cold shock protein.

DNA as a template means the DNA which can serve as a template for the DNA extension when primer anneals to such DNA. The mixture for the method of the present invention can comprise single template or plural templates having different sequences. Using primer pairs for specific templates, respectively, products corresponding to each template can be obtained simultaneously. Such plural templates may be present in same DNA or different DNA molecule. DNA as a template may be double-strand DNA, single-strand DNA or DNA-RNA hybrid.

The amount of cold shock protein used in the present invention is not particularly limited, and it may be more than 0.5 µg, preferably 2 to 15 µg, more preferably 5 to 12 µg, per 25 µl of the reaction mixture.

The amount of DNA polymerase used in the present invention is not particularly limited. For example, it may be the same amount used in the conventional DNA synthesis. The preferred amount of the DNA polymerase for the PCR is known in the skilled artisan. Usually, 0.125 to 5 U of DNA polymerase per 25 µl of the reaction mixture is used in the case of PCR using DNA polymerase derived from *Thermus aquaticus*.

In the present application, activities of the commercially available DNA polymerases are represented on the basis of the indicated units in instruction manual for each DNA polymerase product. For example, activities of the DNA polymerases are determined by using the mixture having a final volume of 50 µl comprising 25 mM TAPS (pH 9.3 at 25° C.), 50 mM potassium chloride, 2 mM magnesium chloride, 1 mM beta-mercaptoethanol, 200 µM each of dATP, dGTP and dTTP, and 100 µM [alpha-32P] dCTP. One unit (hereinafter described as "1 U") of DNA polymerase activity is defined as "an amount of enzyme capable of incorporating 10 nmol of dNTPs into acid-insoluble substances per 30 minutes at 74° C.".

The amount of each primers used in the method of present invention is not particularly limited, it may be 0.05 to 2 µM.

In the preferred embodiment of the present invention, the DNA synthesis is performed by DNA amplification methods, such as PCR.

(3) Kit for the Improved Synthesis of DNA Using DNA Polymerase According to the Present Invention A kit according to the present invention comprises a cold shock protein and a DNA polymerase. There are no particular limitations for the kit of the present invention as long as it is usable in above DNA synthesis method. It may be a kit for labeling nucleic acid, a kit for PCR, a kit for estimation of the nucleic acid, a kit for the site-directed mutagenesis and the like.

The kit of the present invention may further comprises at least one primer, at least one deoxyribonucleotide triphosphate, and/or a reaction buffer solution in addition to cold shock protein and DNA polymerase. As the component of the kit (cold shock protein, DNA polymerase, primer, deoxyribonucleotide triphosphate, and/or reaction buffer solution), ones described in item (1) above can be used.

The kit may comprise above components in a state where each component is present as an independent component, or a state in which some of the components are combined. In one embodiment, the kit of the present invention comprises the composition of the present invention described in above (1).

4) Composition for Improved cDNA Synthesis Using Reverse Transcriptase According to the Present Invention A composition according to the present invention comprises a cold shock protein and a reverse transcriptase. Surprisingly, the reactivity of a reverse transcription reaction was improved in the case where a reaction composition comprising the cold shock protein and the reverse transcriptase was used therein in comparison to a reverse transcription reaction wherein the reverse transcriptase alone was used.

The improvement detected in the reactivity of the reverse transcription reaction is not particularly limited; however, it is selected from the improvement of a reaction specificity, increase in an amount of a nucleic acid synthesis, and increase of length of the synthesized strand. The present invention is advantageous particularly for a reverse transcription reaction for synthesis of long-stranded cDNA, and results increase in an amount of cDNA synthesized. Further, the synthesis of non-specific cDNA can be reduced. It was conventionally believed that a reverse transcription reaction at high temperatures using a heat-resistant reverse transcriptase was effective for the synthesis of the long-stranded cDNA (for example, see WO 01/92500). According to the present invention, the long-stranded cDNA can be efficiently synthesized without carrying out the reverse transcription reaction at high temperature. The present invention is also applicable to the reverse transcription reaction at high temperatures, and the reverse transcription reactions in which various enzymes are used can be accordingly improved.

Possible actions of the CspA expected in the composition according to the present invention are the improvement of a reaction specificity and increase of the amount of amplified product resulting from the suppression of mispriming at low temperatures, and the improvement of extension and increase of the amount of amplified product obtained by the dissolution of a two-dimensional structure of RNA.

Any reverse transcriptase can be used in the present invention as far as it has a reverse transcription activity, that is an activity for synthesizing DNA complementary to RNA used as a template. Examples of the reverse transcriptase are reverse transcriptases derived from viruses such as a reverse transcriptase derived from Moloney Murine Leukemia Virus (reverse transcriptase derived from MMLV), a reverse transcriptase derived from Avian Myeloblastosis Virus (reverse transcriptase derived from AMV), and reverse transcriptases derived from eubacteria such as DNA polymerase derived from bacterium of the genus *Thermus* (Tth DNA polymerase, and the like) and DNA polymerase derived from thermophilic bacterium of the genus *Bacillus* (Bca DNA polymerase, and the like).

The reverse transcriptases derived from viruses are preferably used, and the reverse transcriptase derived from MMLV is more preferably used in the present invention. Further, a reverse transcriptase modified into a naturally-derived amino acid sequence can also be used in the present invention as far as it has the reverse transcription activity.

The composition according to the present invention may include at least one primer, at least one deoxyribonucleotide, and/or a reaction buffer solution in addition to the cold shock protein and the reverse transcriptase.

The primer may be an oligonucleotide having a nucleotide sequence complementary to the template RNA, and is not particularly limited as long as it anneals to the template RNA under the reaction conditions used. The primer may be oligonucleotide such as oligo (dT) or oligonucleotide having a random sequence (random primer).

A length of the primer is preferably at least six nucleotides since a specific annealing process is performed, and more preferably at least 10 nucleotides. The length of the primer is preferably at most 100 nucleotides and more preferably at most 30 nucleotides in terms of the synthesis of oligonucleotide. The oligonucleotide can be synthesized, for example, according to the phosphoramidite method by the DNA synthesizer 394 (manufactured by Applied Biosystems Inc). The oligonucleotide may be synthesized according to any other process, such as the triester phosphate method, H-phosphonate method, or thiophosphate method. The oligonucleotide may be oligonucleotide derived from a biological specimen, and for example, may be prepared such that it is isolated from restricted endonuclease digest of DNA prepared from a natural specimen.

Each of the compositions for reverse transcription reaction including the cold shock protein and a reactant accelerator for reverse transcription reaction including the cold shock protein is also involved as an embodiment in the present invention.

5) Process for Improved cDNA Synthesis Using Reverse Transcriptase According to the Present Invention The present invention provides a process for synthesizing cDNA, wherein a composition according to the present invention is used, comprises the steps of:
A) preparing a solution comprising a cold shock protein, a reverse transcriptase, at least one primer, at least one deoxyribonucleotide, and RNA serving as a template; and
B) incubating the solution prepared in the step A).

According to this cDNA synthesis process of the present invention, the reactivity of the reverse transcription reaction is improved in comparison to a process wherein a composition not comprising the cold shock protein is used.

The improvement of the reactivity of the reverse transcription reaction can evaluated by, for example, the examination of the amount and the strand length of the synthesized cDNA.

The amount of synthesized cDNA obtained by the reverse transcription reaction can be examined such that a certain quantity of the reaction solution after the reverse transcription reaction is subjected to a real time PCR so that an amount of synthesized targeted nucleic acid sequence is quantified. In the case where the reverse transcription reaction is performed with a composition according to the present invention, the amount of synthesized cDNA is increased in comparison to the case where a composition not including the cold shock protein is used in the reverse transcription reaction.

The length of the synthesized cDNA obtained by the reverse transcription reaction can be confirmed by determining the amounts of the amplification products obtained in PCR using a pair of primer in different pairs of primers having different amplification strand lengths from the downstream vicinity of a priming region of the primer used in the reverse transcription reaction, and a certain quantity of the reaction solution after the reverse transcription reaction. In the case where the composition according to the present invention is used in the reverse transcription reaction, the amount of the long-stranded cDNA synthesized is increased in comparison to the case where the composition not including the cold shock protein is used in the reverse transcription reaction.

The RNA as the template is RNA which can serve as a template of the reverse transcription reaction from the primer when the primer is hybridized to it. The composition according to the present invention may include one kind of template or a plurality of different templates having different nucleotide sequences. When a specific primer for a particular template is used, primer extension products from the plurality of different templates in the nucleic acid mixture can be produced. The plurality of templates may be present in the different nucleic acids or the same nucleic acid.

The RNA, which is a template to which the present invention is applicable, is not particularly limited. Examples of the RNA are an group of RNA molecules in all of RNAs in a specimen, a group of RNA molecules such as mRNA, tRNA, and rRNA, or particular group of RNA molecules (for example, a group of RNA molecules having a common nucleotide sequence motif, a transcript by the RNA polymerase, a group of RNA molecules concentrated by means of the subtraction process), and an arbitrary RNA capable of producing the primer used in the reverse transcription reaction.

In the present invention, the RNA serving as the template may be included in a specimen derived from an organism such as cells, tissues or blood, or a specimen such as food, soil or waste water which possibly includes organisms. Further, the RNA may be included in a nucleic acid-containing preparation obtained by processing such a specimen or the like according to the conventional process. Examples of the preparation is homogenized cells, and a specimen obtained by fractioning the homogenized cells, all of RNAs in the specimen, or a group of particular RNA molecules, for example, a specimen in which mRNA is enriched, and the like.

The amount of the cold shock protein to be used in the process according to the present invention is not particularly limited. In the case where the reverse transcription reaction is performed with 20 μL of the reaction solution, the amount is preferably 0.5-20 μg, more preferably 1-10 μg, and even more preferably 2-5 μg.

The amount of the reverse transcriptase to be used in the process according to the present invention is not particularly limited. For example, the amount used in the conventional reverse transcription reaction may be used. In the case of the reverse transcription reaction wherein the reverse transcriptase derived from MMLV and 20 μL of the reaction solution are used, for example, the amount of the reverse transcriptase in the reaction solution is preferably at least 10 U, and more preferably at least 100 U and even more preferably at least 200 U in view of an efficiency in the cDNA synthesis. In the conventional process, it was necessary to adjust the amount of the reverse transcriptase in accordance with the amount of the template RNA and the length of the cDNA synthesized in order to avoid any possible inhibition occurred by excess amount of the reverse transcriptase, however, such an adjustment is unnecessary in the process according to the present invention.

The activity of the reverse transcriptase recited in the specification of the present invention is based on that of any reverse transcriptase commercially available. For example, 1 U is the activity of the enzyme that incorporates 1 nmol of [$^3$H]dTTP in 10 minutes at 37° C., with Poly (rA)•oligo (dT)$_{12-18}$ is used as the primer-template.

The concentration of the primer used in the process according to the present invention is not particularly limited. The concentration is preferably at least 0.1 μM in the case where a specific primer is used in the reverse transcription reaction, preferably at least 2.5 μM in the case where an Oligo dT primer is used in the reverse transcription reaction, and preferably at least 5 μM in the case where a random primer is used in the reverse transcription reaction in order to maximize the cDNA synthesis from the template RNA. In the conventional process, it was necessary to adjust the amount of the primer in accordance with the amount of the template RNA and the length of the cDNA synthesized in order to avoid any possible inhibition occurred in the reverse transcription reaction by excess amount of the primer is too large, however, such an adjustment is unnecessary in the process according to the present invention.

The cDNA synthesis process according to the present invention suitably includes:

A) a step of preparing a reaction composition by mixing CspA, a reverse transcriptase, at least one ribonucleotide, at least one primer, and RNA serving as a template; and B) a step of incubating the reaction composition prepared in the step A) under conditions satisfactory for synthesizing a primer extension strand complementary to the template RNA.

The conditions which are satisfactory for synthesizing the primer extension strand complementary to the template RNA are not particularly limited. An example of a temperature range may be 30° C.-65° C., preferably 37-50° C., and 42° C.-45° C. is more preferable. An example of a preferable reaction time period is 5 min.-120 min., and 15 min.-60 min. is more preferable. According to the cDNA synthesis process of the present invention, the synthesis of a non-specific primer extension strand, which is generated when the reaction solution is left at any temperature failing to satisfy the foregoing temperature ranges, can be controlled or reduced. Therefore, the cDNA synthesis process according to the present invention is particularly advantageous in, for example, the synthesis of cDNA which demands a long period of time to prepare the reaction solutions since a number of the samples to be examined are handled.

When a nucleic acid amplification reaction, wherein the cDNA obtained by the process according to the present invention is used as a template, is performed, the cDNA can be amplified. The nucleic acid amplification reaction is not particularly limited. A preferable example thereof is the polymerase chain reaction (PCR).

6) Kit for Improved cDNA Synthesis Using Reverse Transcriptase According to the Present Invention The kit according to the present invention comprises the cold shock protein and the reverse transcriptase. According to the kit of the present invention, the reverse transcription reaction capable of achieving a high reactivity can be realized. The kit according to the present invention is not particularly limited as far as it is designed to be used for the reverse transcription reaction. A preferable example is a kit used for performing the reverse transcription reaction in vitro. More specific examples are a kit for nucleic acid labeling, a kit for RT-PCR, a kit for cDNA synthesis, a kit for introduction of site-directed mutagenesis.

The kit according to the present invention may include, in addition to the cold shock protein and the reverse transcriptase, at least one primer, at least one deoxyribonucleotide, nucleic acid as a template and/or a reaction buffer solution.

Referring to the cold shock protein, reverse transcriptase, at least one primer, at least one deoxyribonucleotide, nucleic acid as a template and/or reaction buffer solution, a part or all of them may be included as mixture in the kit, or they may be separately included in the kit as a single component each.

The kit according to the present invention may further include a reagent for performing a gene amplification reaction in which the cDNA obtained by the reverse transcription reaction is used as a template, for example, PCR. Examples of the reagent are heat-resistant DNA polymerase, reaction buffer solution, at least one deoxyribonucleotide, and at least a pair of primers.

Examples of the cold shock protein, reverse transcriptase, at least one primer, at least one deoxyribonucleotide, nucleic acid as a template and/or reaction buffer solution included in the kit according to the present invention are as previously described above.

(7) Composition for Identifying Endoribonuclease Cleavage-Sites According to the Present Invention A composition according to the present invention comprises a cold shock protein, an RNA substrate, and an endoribonuclease. In determining cleavage specificity of endoribonucleases that recognize a specific sequence longer than three bases, it is essential to use an RNA substrate that is long enough to cover all possible target sequences; for example RNA substrate should be longer than 1024 bases ($=4^5$) to contain all possible five base cleavage sites, assuming the RNA contains an equal number of each base. Preferably, bacteriophage MS2 RNA may be used, consisting of 3569 bases and having a fairly even base content (26% G, 23% A, 26% C and 25% U) as the substrate for the determination of cleavage specificity.

Figure 14A:
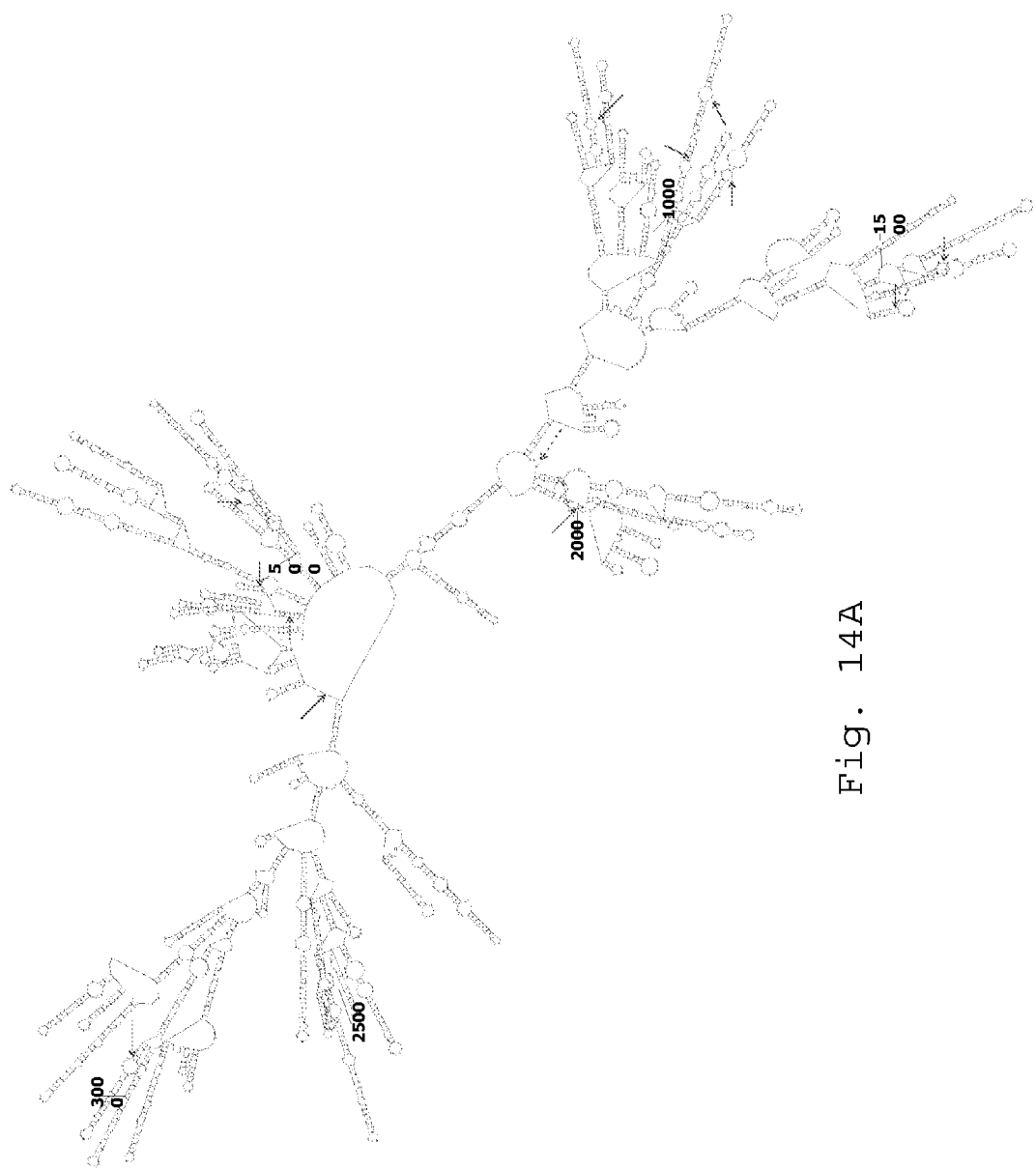
FIG. 14A depicts the predicted secondary structure of MS2ssRNA by MFOLD (http://bioweb.pasteur.fr/seqanal/interfaces/mfold-simple.html). Minimum Folding Energy at 37° C. is −1460.69 kcal/mole. The arrows indicate cleavage sites of MazF-mt3 identified by primer extension analysis and the blue dotted arrow indicates the predicted cleavage sites of MazF-mt3 that were not detected by primer extension analysis.

A major problem in using such long RNAs as a substrate, however, is that although it is a single-stranded RNA, it forms extensive stable secondary structures (see FIG. 14A), which can impede cleavage. Therefore, in order to use such long RNAs as substrate for endoribonucleases, their secondary structures have to be unfolded.

The present invention employs cold shock proteins to unfold the secondary structures of these long RNA substrates. By unfolding these secondary structures, cold shock proteins increase the amount of RNA that is available to be cleaved, thus aiding in determining endoribonuclease cleavage sites. Preferably, the concentration of cold shock protein is at least 0.43 mM or is otherwise sufficient for completely saturating the RNA substrate.

mRNA interferases are an example of an endoribonuclease which may be employed in the present invention, but such endoribonucleases are not particularly limited as long as they are capable of cleaving single stranded RNA.

(8) Method for Identifying Endoribonuclease Cleavage-Sites According to the Present Invention Another method for identifying endoribonuclease cleavage sites according to the present invention comprises the steps of:

A) preparing a mixture comprising a cold shock protein, an RNA substrate, and an endoribonuclease; and B) incubating the mixture prepared in step A).

By this method of the present invention, the cleavage specificity of endoribonucleases can be determined. The cold shock protein enhances cleavage of the RNA substrate by the endoribonuclease by preventing formation of secondary structures in the RNA.

Preferably, the mixture is incubated at 37° C. for 15 minutes. The cleavage sites may be analyzed in vitro by primer extension analysis, as described in Example 17.

(9) Kit for Identifying Endoribonuclease Cleavage Sites According to the Present Invention A kit according to the present invention comprises a cold shock protein and an RNA substrate. According to the kit of the present invention, the cleavage sites of an endoribonuclease may be determined by incubating an endoribonuclease of interest with the components of the kit. The kit according to the present invention is not particularly limited as far as it is designed to be used for identifying endoribonuclease cleavage sites.

EXAMPLES

The following Examples illustrate the present invention in more detail, but are not to be construed to limit the scope thereof. The activities of respective reverse transcriptases recited in the following examples are shown based on the instruction manual attached to the respective reverse transcriptases.

Preparation Examples

Preparation of CspA Solution and Enzyme Storage Buffer

CspA was expressed and purified according to the method described in "Journal of Biochemistry (J. Biochem.) by S. Chatterjee et al., 1993, 114, 663-669", and then, a 2 µg/µL CspA solution (2 µg/µL CspA, 20 mM of Tris-HCl (pH 7.8 (4° C.), 100 mM of NaCl, 1 mM of EDTA, 1 mM of DTT, and 50% Glycerol), a 5 µg/µL CspA solution (5 µg/µL CspA, 20 mM of Tris-HCl (pH 7.8 (4° C.), 100 mM of NaCl, 1 mM of EDTA, 1 mM of DTT, and 50% Glycerol), and a 14.8 µg/µL CspA solution [14.8 µg/µL CspA, 20 mM of Tris-HCl (pH 7.8 at 4° C.), 100 mM of NaCl, 1 mM of EDTA, 1 mM of OTT, and 50% Glycerol] were prepared.

Further, an enzyme storage buffer not including CspA (20 mM of Tris-HCl (pH 7.8 (4° C.), 100 mM of NaCl, 1 mM of EDTA, 1 mM of DTT, and 50% Glycerol) was prepared.

As an enzyme storage buffer recited in the following examples, the enzyme storage buffer prepared in the foregoing preparation example was used. As a CspA solution, the 2 µg/µL CspA solution prepared in the foregoing preparation example was used in the examples 6-11, the 5 µg/µL CspA solution prepared in the foregoing preparation example was used in the examples 12-13, and the 14.8 µg/µL CspA solution prepared in the foregoing preparation example was used in examples 1-5.
Strains and Plasmids E. coli BL21 (DE3) strain was used for recombinant protein expression. Plasmid pET-28a-MazF-mt3 and -mt7 were constructed from pET-28a (Novagen) to express (His)$_6$ MazF-mt3, and -mt7, respectively.
Purification of (His)$_6$ Tagged MazF-mt3 and MazF-mt7 in E. coli MazF-mt3 and MazF-mt7 (His)$_6$ tagged at the N-terminal end were purified from strain BL21(DE3) carrying pET-28a-MazF-mt3 and MazF-mt7 using Ni-NTA resin (Qiagen).

Example 1

PCR mixtures having a final volume of 25 micro 1 comprising 5 ng or 50 ng of Human genome DNA (manufactured by Clontech Laboratories, Inc.), 10 pmol each of forward primer (SEQ ID NO: 1) and reverse primer (SEQ ID NO: 2) for amplification of 2 kb DNA fragment of p53 gene, 0.625 U of TaKaRa Taq (Tag DNA polymerase; manufactured by TAKARA BIO INC.) were prepared on the ice by using reaction buffer attached to TaKaRa Taq in accordance with the instruction manual for TaKaRa Taq. 2, 4, 6, 8, 10, 12 or 14 µg of CspA was respectively added to the above mixtures. Also, the mixture which does not contain CspA was prepared as a control.

Each mixtures thus prepared were incubated at 25° C. for 30 min. Then PCR was carried out in 30 cycles, wherein one cycle comprises a process consisting of 98° C., 10 seconds-55° C., 30 seconds-72° C., 2 minutes. After termination of the reaction, 3 µl of each sample was electrophoresed on 1% agarose gel, and the lengths and amounts of amplified products in each mixture were determined.

As shown in FIG. 1, the product of 2 kb in length was not found and the products of various lengths due to the non-specific amplification were observed in the mixture not containing CspA. On the contrary, the 2 kb product was clearly observed in each mixtures containing 4 to 14 µg of CspA, respectively. The amounts of the product in the mixtures containing 6 to 10 µg of CspA were larger than other mixtures. The result clarified that CspA reduces non-specific amplification arising from leaving of the mixture at room temperature before PCR.

Example 2

Figure 2:
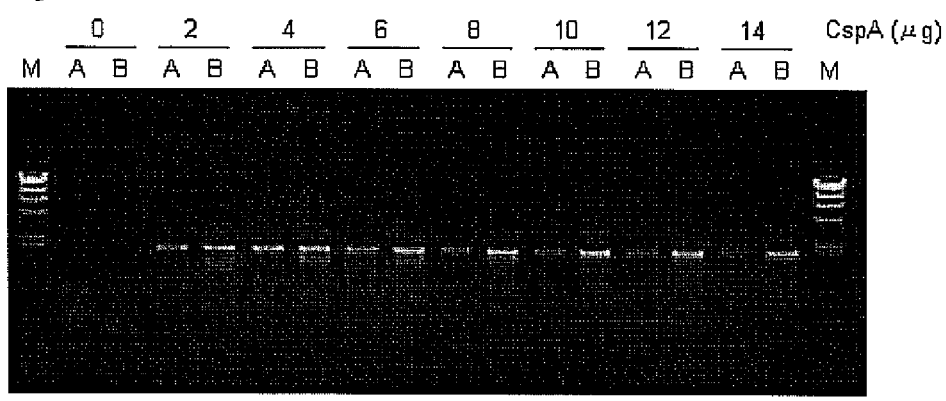
FIG. 2 illustrates the result of agarose gel electrophoresis of DNA fragment amplified by DNA polymerase mixture for LA-PCR in the presence or in the absence of CspA. HindIII-digested lambda DNAs are electrophoresed in the lanes marked with "M".

Further, the same experiment was conducted as described in Example 1 except that the DNA polymerase was changed from TaKaRa Taq to TaKaRa Ex Taq (DNA polymerase mixture for LA-PCR: manufactured by TAKARA BIO INC.). Essentially the same result was obtained by using DNA polymerase mixture for LA-PCR. The increase in the amounts of the product was observed in the mixtures containing 6 µg CspA or more (see FIG. 2).

Example 3

PCR mixtures having a final volume of 25 µl comprising 5 ng or 50 ng of Human genome DNA (manufactured by Clontech Laboratories, Inc.), 10 pmol each of forward primer (SEQ ID NO: 1) and reverse primer (SEQ ID NO: 2) for amplification of 2 kb DNA fragment of p53 gene, 0.625 U of Pyrobest DNA polymerase (alpha-type DNA polymerase: manufactured by TAKARA BIO INC.) were prepared on the ice by using reaction buffer attached to Pyrobest DNA polymerase in accordance with the instruction manual for Pyrobest DNA polymerase. 0.5, 1, 2, 4, 6, 8, 10, 12 or 14 µg of CspA was respectively added to above mixtures. Also, the mixture which does not contain CspA was prepared as a control.

Figure 3:
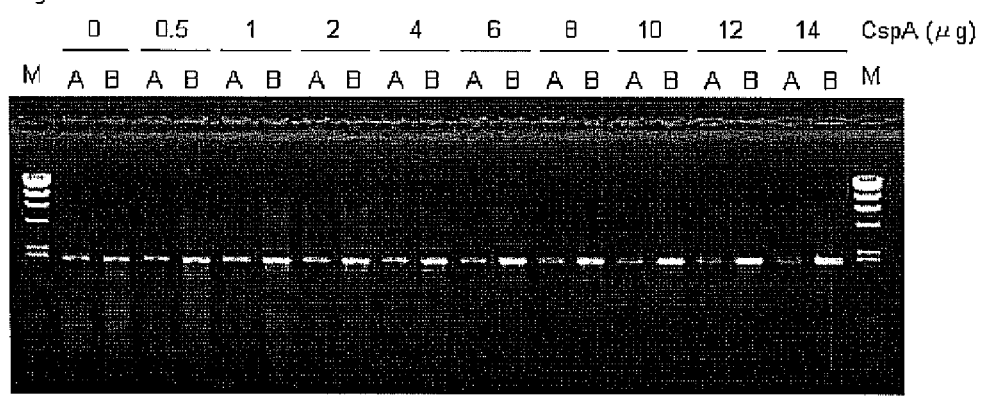
FIG. 3 illustrates the result of agarose gel electrophoresis of DNA fragment amplified by alpha-type DNA polymerase in the presence or in the absence of CspA. HindIII-digested lambda DNAs are electrophoresed in the lanes marked with "M".

Each mixtures thus prepared were incubated at 25° C. for 30 min. Then PCR was carried out in 30 cycles, wherein one cycle comprises a process consisting of 98° C., 10 seconds-60° C., 30 seconds-72° C., 2 minutes. After termination of the reaction, 3 µg of each sample was electrophoresed on 1% agarose gel, and the lengths and amounts of an amplified product in each mixture were determined. The result was shown in FIG. 3.

In the mixture not containing CspA, significant amount of the products of various length were observed in addition to the product of 2 kb in length. The non-specific amplification observed in the absence of CspA was reduced, and the amounts of the 2 kb products were increased in the mixtures containing 2 µg of CspA or more.

The result showed that CspA also reduces the non-specific amplification in PCR using alpha-type DNA polymerase.

Example 4

PCR mixtures having a final volume of 25 µg comprising 50 ng of Human genome DNA, 0.625 U of TaKaRa ExTaq, 10 µg of CspA and primer pair for amplifying 575 bp fragment of TP53 gene (SEQ ID NOS: 3 and 4), 591 bp fragment of Bcl2 gene (SEQ ID NOS: 5 and 6), 521 bp fragment of EGFR gene (SEQ ID NOS: 7 and 8), 380 bp fragment of CDK9 gene (SEQ ID NOS: 9 and 10), 1010 bp fragment of FFAR2 gene (SEQ ID NOS: 11 and 12), 520 bp fragment of IRS1 gene (SEQ ID NOS: 13 and 14) or 460 bp fragment of GAP gene (SEQ ID NOS: 15 and 16), respectively, were prepared on the ice by using reaction buffer attached to TaKaRa ExTaq in accordance with the instruction manual for TaKaRa ExTaq. The mixtures which do not contain CspA were also prepared as a control.

Each mixture thus prepared were subjected to PCR in 30 cycles under two different conditions. In condition 1, one cycle comprises a process consisting of 98° C., 10 seconds-53° C., 30 seconds-72° C., 30 seconds. In condition 2, one cycle comprises a process consisting of 98° C., 10 seconds-60° C., 30 seconds-72° C., 30 seconds. After termination of the reaction, 3 µg of 10 each mixture was electrophoresed on 1% agarose gel, and the amplified products in mixtures were analyzed.

Figure 4:
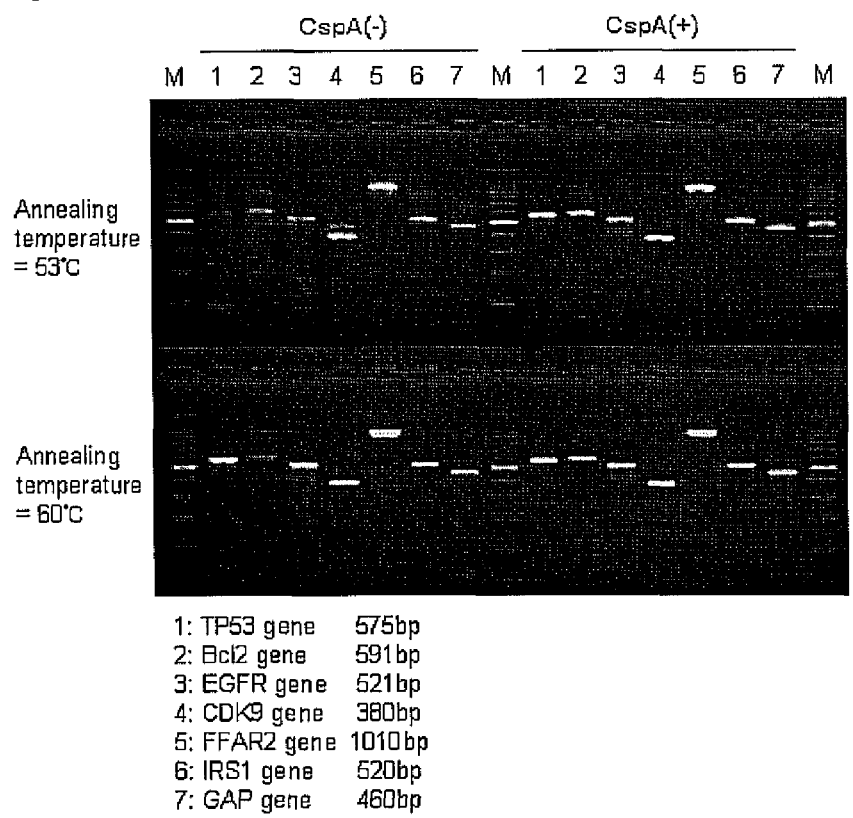
FIG. 4 illustrates the result of agarose gel electrophoresis of DNA fragment amplified from various target sequence in the presence or in the absence of CspA. 100 bp ladder markers (manufactured by TAKARA BIO INC) are electrophoresed in the lanes marked with "M".

All of the primers used in above reaction have the Tm value exceeding 70° C., therefore, they are prone to cause the non-specific amplification. Actually, the specificities of the amplification under condition 1 were significantly low in the absence of CspA. In the presence of CspA, however, only the expected product was observed in each mixture amplified under condition 1 and 2 (see FIG. 4).

This result shows that CspA have the ability of increasing the specificity of PCR amplification, and it can expand the range of annealing temperature for specific amplification of nucleic acids Example 5

Figure 5:
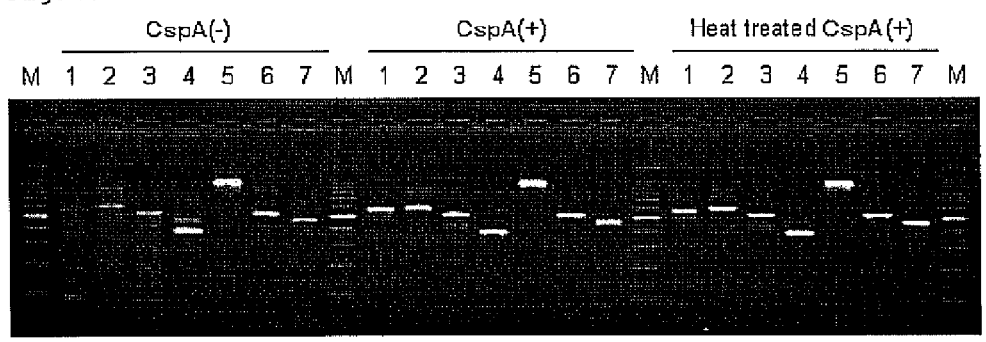
FIG. 5 illustrates the result of agarose gel electrophoresis of DNA fragment amplified by DNA polymerase mixture for LA-PCR in the presence of heat-treated or non heat-treated CspA. 100 bp ladder markers are electrophoresed in the lanes marked with "M".

Two aliquots of solution comprising 10 µg/ml CspA were prepared, and one of them was treated at 98° C. for 5 minutes. PCR mixtures having same composition shown in Example 4, but comprising 10 µg of heat-treated or non heat-treated CspA thus prepared were prepared. Each mixtures thus prepared were subjected to PCR in 30 cycles under condition 1. Upon examining the amplified products in each mixture after termination of the reaction, no difference was observed between heat-treated and non heat-treated CspA. The result was shown in FIG. 5. This result suggests the high thermostability of CspA.

Example 6

Confirmation of Amount of Non-Specific Extension Product (Background) from Other than PolyA in Reverse Transcription Reaction Using Oligo dT as a Primer 20 µL of a reverse transcription reaction solution for synthesizing cDNA was prepared on ice using PrimeScript (registered trademark) RTase (manufactured by TAKARA-BIO INC.) wherein 1 µg of Human heart total RNA (manufactured by Clontech) as a template and Oligo dT (final concentration 2.5 µM) were used. In the composition of the reverse transcription reaction solution prepared then, 2 µg CspA was included in addition to the composition of the reverse transcription reaction solution recited in the instruction manual attached to PrimeScript (registered trademark) RTase. As a control, a reverse transcription reaction solution not including CspA in which 1 µL of the enzyme storage buffer is added in place of CspA was also prepared. Next, these reverse transcription reaction solutions thus prepared on ice were left on ice for 0-20 minutes, and thereafter heated to 95° C. so that the reverse transcriptases were inactivated. Then, in order to confirm the amount of cDNA generated in each of the solutions left on ice for 0-20 minutes, 2 µL of the respective reaction solutions were subjected to a real time PCR which targets the strand of 139 bases (6529-6667) in length in a region distant from PolyA of a dystrophin gene (GenBank Accession Number NM_004006) by approximately 7 kb, and the strand of 6,930 bases (6529-13458) in length from the vicinity of PolyA.

The real time PCR which targets the 139 bases was performed using SYBR (registered trademark) Premix Ex Taq (manufactured by TAKARABIO INC.) based on recommended conditions in the instruction manual attached thereto, wherein a primer having the nucleotide sequence shown in SEQ ID NO: 17 and a primer having the nucleotide sequence shown in SEQ ID NO: 18 were used as the primers. The long-strand real time PCR which targets the 6,930 bases was performed using PrimeSTAR (registered trademark) GXL (manufactured by TAKARABIO INC.) and SYBR (registered trademark) Green I (manufactured by TAKARABIO INC.), wherein a primer having the nucleotide sequence shown in SEQ ID NO: 17 and a primer having the nucleotide sequence shown in SEQ ID NO: 19 were used as the primers. The reaction solutions for the real time PCR were prepared in accordance with a reaction solution composition of high-speed PCR protocols recited in the instruction manual attached to PrimeSTAR (registered trademark) GXL except that SYBR (registered trademark) Green I was added so that the final concentration will be ×0.33. Further, the real time PCR was performed, after the incubation for 10 seconds at 98° C., under the condition of 40 cycles in which 98° C. for five seconds –68° C. for two minutes constitutes one cycle. In any of the reverse transcription examples recited in this specification, Thermal Cycler Dice (registered trademark) Real time system TP 800 (manufactured by TAKARABIO INC.) was used for the real time PCR. Further, standard curves were generated by means of a serial dilution of plasmid in which cDNA of 13,542 bases (173-13714) including the foregoing regions were cloned to the Hinc II site of pUC118.

Figure 6:
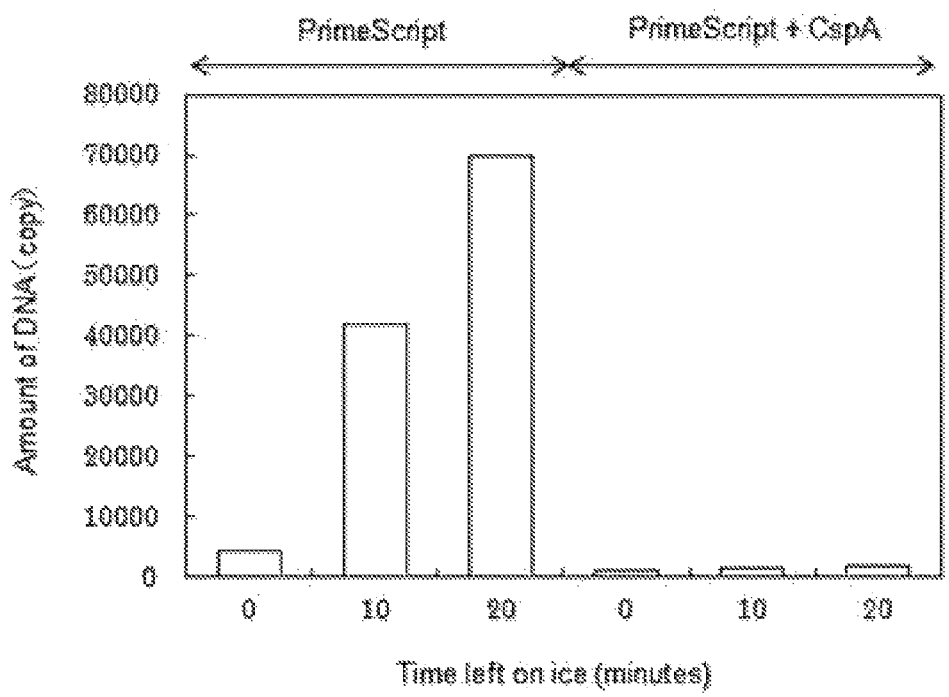
FIG. 6 is a drawing illustrating an effect exerted by CspA for inhibiting non-specific extension products.

As a result, long-stranded cDNA products of 6,930 bases from the vicinity of PolyA were not detected irrespective of the presence or absence of CspA in the reverse transcription reactions. The amount of cDNA of 139 bp in the region distant from PolyA by approximately 7 kb was increased in the solution which did not include CspA therein as the solution was left on ice longer. In the case of the reverse transcription solution including CspA, the amount of cDNA in the same region hardly increased, and the amount of synthesized cDNA in the solution left on ice for 20 minutes was ¹⁄₄₀ of that of the reaction solution not including CspA (FIG. 6). Since the long-stranded cDNA products of 6,930 bases from the vicinity of PolyA were not found, it is indicated that the cDNA products of 139 bp in the region distant from PolyA by approximately 7 kb when the reverse transcription reaction solution was prepared and left on ice were not the products extended from PolyA but non-specific extension products from other than PolyA. Such a non-specific extension product can be a background in obtaining cDNA having a full length. The non-specific extension product inhibits the extension reaction from PolyA to the 5' end of RNA, and increases cDNA synthesis products not having a full length.

In the present example, it was confirmed that the synthesis of the non-specific extension product (background) from other than PolyA when the reverse transcription reaction solution was prepared and left on ice was almost completely suppressed by CspA in the reverse transcription reaction solution.

Example 7

Confirmation of Amount of Non-Specific Extension Product (Background) from Other than PolyA in Reverse Transcription Reaction Using Oligo dT as a Primer The effect of CspA was confirmed according to a process similar to that of the example 6 except that 20 µL of a reverse transcription reaction solution including 2 µg CspA and 20 µL of the reverse transcription reaction solution not including CspA were prepared using SuperScript III RTase (manufactured by Invitrogen Corporation) based on the instruction manual attached thereto in place of PrimeScript (registered trademark) RTase. SuperScript III RTase is a variant of the reverse transcriptase derived from MMLV.

Figure 7:
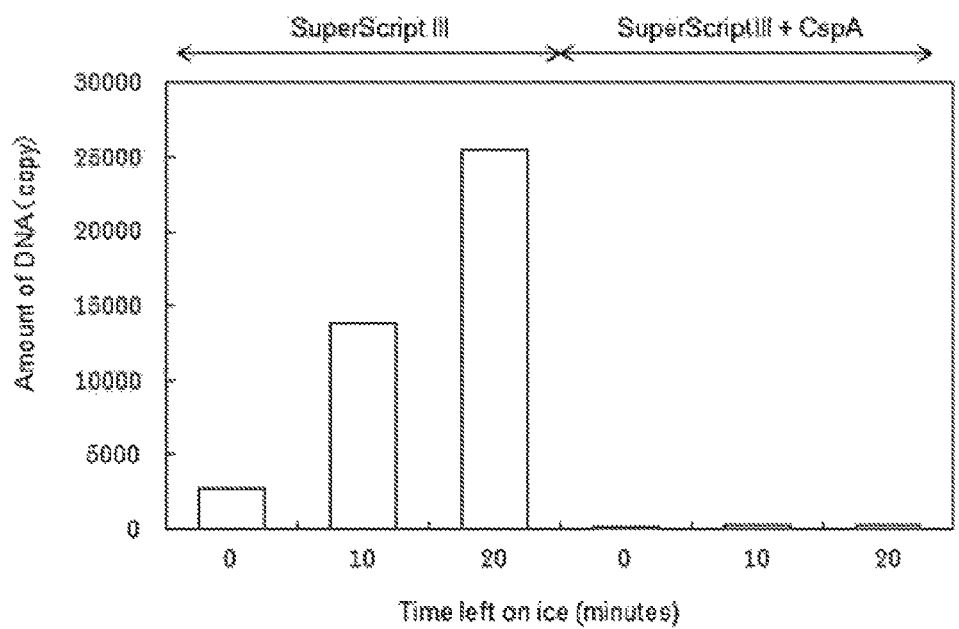
FIG. 7 is a drawing illustrating an effect exerted by CspA for inhibiting non-specific extension products.

As a result, long-stranded cDNA products of 6,930 bases from the vicinity of PolyA were not detected irrespective of the presence or absence of CspA in the case where SuperScript III RTase was used as the reverse transcriptase. The amount of synthesized cDNA of 139 bp in the region distant from PolyA by approximately 7 kb was increased in the solution which did not include CspA therein as the solution was left on ice longer. In the case of the reverse transcription solution including CspA, the amount of cDNA in the same region hardly increased, and the amount of synthesized cDNA in the solution left on ice for 20 minutes was 1/87 of that of the reaction solution not including CspA (FIG. 7). Thus, it was confirmed that the synthesis of the non-specific extension product (background) from other than PolyA when the reverse transcription reaction solution was prepared and left on ice was almost completely suppressed by CspA in the reverse transcription reaction solution though SuperScript III RTase was used as the reverse transcriptase.

Example 8

Confirmation of Amount of Non-Specific Extension Product (Background) from Other than PolyA in Reverse Transcription Reaction Using Oligo dT as a Primer The effect of CspA was confirmed according to a process similar to that of the example 6 except that 20 µL of a reverse transcription reaction solution including 1 µL of 1 µg/µL Human heart total RNA (manufactured by Clontech), 1 µL of 50 µM Oligo dT, 1.6 µL of each 2.5 mM dNTP mixture, 2 µL of Reverse Transcriptase XL (AMV) Buffer, 0.5 µL of 40 U/µL Ribonuclease Inhibitor, 0.8 µL of 25 U/µL Reverse Transcriptase XL (AMV) and 14 of 2 µg/µL CspA, and 20 µL of a reverse transcription reaction solution not including CspA were prepared using Reverse Transcriptase XL (AMV) (manufactured by TAKARABIO INC.) in place of PrimeScript (registered trademark) RTase. The Reverse Transcriptase XL (AMV) is a reverse transcriptase derived from AMV.

Figure 8:
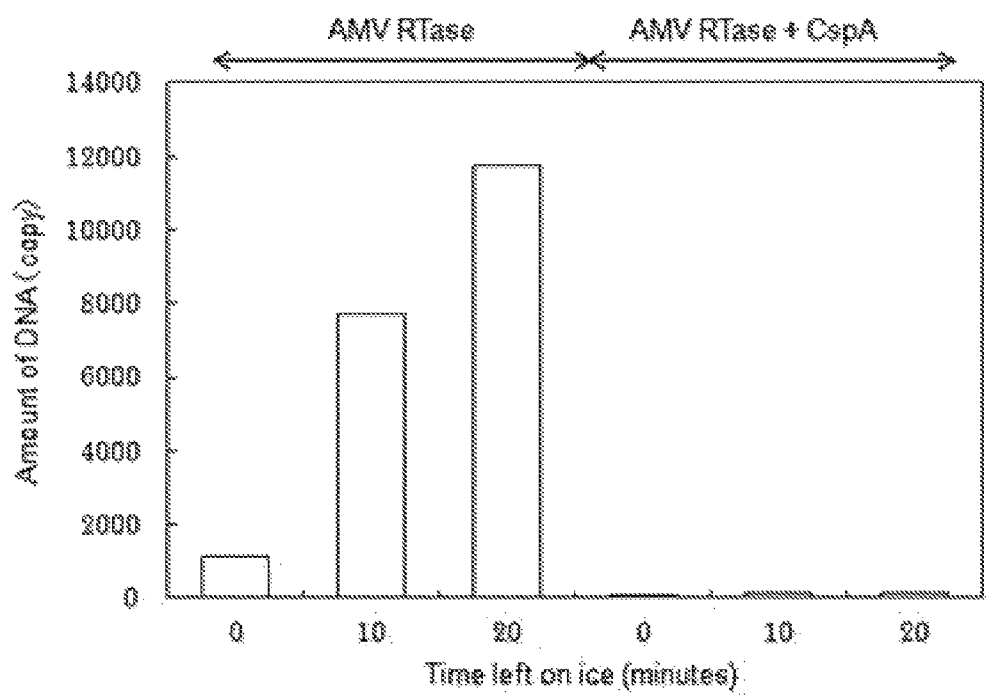
FIG. 8 is a drawing illustrating an effect exerted by CspA for inhibiting non-specific extension products.

As a result, long-stranded cDNA products of 6,930 bases from the vicinity of PolyA were not detected irrespective of the presence or absence of CspA in the reaction solutions in the case where Reverse Transcriptase XL (AMV) was used as the reverse transcriptase. The amount of cDNA of 139 bp in the region distant from PolyA by approximately 7 kb was increased in the solution which did not include CspA therein as the solution was left on ice longer. In the case of the reverse transcription solution including CspA, the amount of cDNA in the same region hardly increased, and the amount of synthesized cDNA in the solution left on ice for 20 minutes was 1/84 of that of the reaction solution not including CspA (FIG. 8). Thus, it was confirmed that the generation of the non-specific extension product (background) from other than PolyA when the reverse transcription reaction solution was prepared and left on ice was almost completely suppressed by CspA in the reverse transcription reaction solution though the reverse transcriptase derived from AMV was used.

Example 9

Inhibition of Long-Stranded cDNA Synthesis Reaction in Reverse Transcription Reaction Using Oligo dT as a Primer 20 µL of a reverse transcription reaction solution including 2 µg CspA and 20 µL of a reverse transcription reaction solution not including CspA were prepared according to a process similar to that of the example 1 using PrimeScript (registered trademark) RTase (manufactured by TAKARA-BIO INC.). The solutions prepared on ice were left on ice for 0-20 minutes and subjected to the reverse transcription reaction at 42° C. for 30 minutes, and then heated at 95° C. for five minutes, and the reaction was stopped. 2 µL of the respective reaction solutions were subjected to the real time PCR which targets the long strands of 6,930 bases from the vicinity of PolyA of a dystrophin gene according to a process similar to that of the example 6, so that the amount of the cDNA synthesized from the reverse transcription reaction was quantified.

Figure 9:
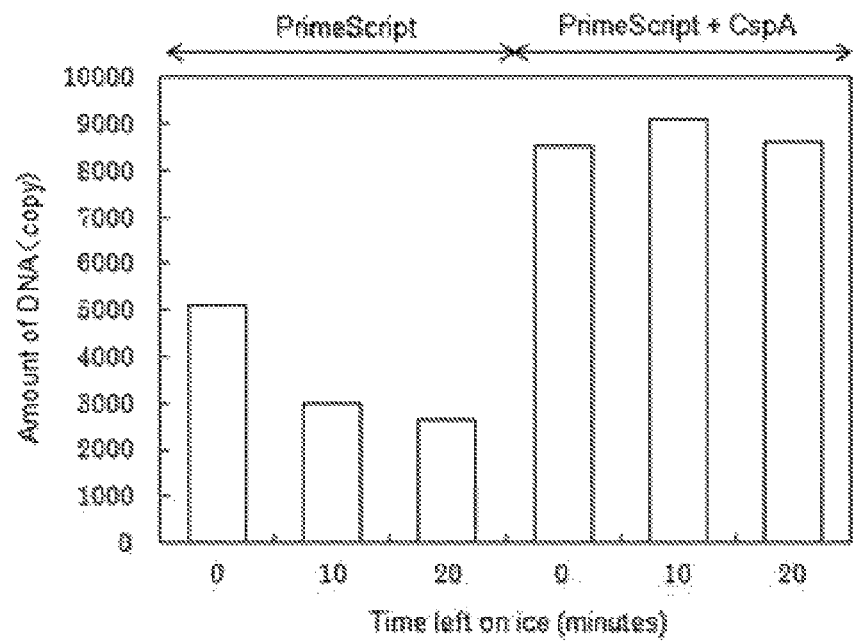
FIG. 9 is a drawing illustrating an effect exerted by CspA for improving reactivity of reverse transcription reaction.

As a result, in the reaction solution not including CspA, the amount of the long-stranded extension products of 6,930 bases from the vicinity of PolyA was reduced to 52% in the case where the solution was left on ice for 20 minutes in comparison to the solution not left on ice at all. In the reaction solution including CspA, the amount of synthesized cDNA was not at all reduced though left on ice for 20 minutes (FIG. 9). It appears that the effect of CspA was obtained because the non-specific extension reaction from other than PolyA was almost completely suppressed by the CspA in the reaction solution, and the extension reaction was not inhibited by PolyA.

It was confirmed from the obtained result that the CspA in the reaction solution makes it unnecessary to mind an amount of time necessary for the reverse transcription reaction after the reaction solution is prepared, and the cDNA synthesis reaction achieving a high quality in which the background is very few in the cDNA synthesis from PolyA and quite possibly having a full length can be realized.

Example 10

Inhibition 2 of Long-Stranded cDNA Synthesis Reaction in Reverse Transcription Reaction Wherein Oligo dT is Used as Primer The test was performed according to a process similar to that of the example 9 except that 20 µL of a reverse transcription reaction solution including 2 µg CspA and 20 µL of a reverse transcription reaction solution not including CspA were prepared using SuperScript III RTase (manufactured by Invitrogen Corporation) in place of PrimeScript (registered trademark) RTase based on the instruction manual attached to SuperScript III RTase, the reverse transcription reaction was performed at 50° C. for 30 minutes, the solutions were heated at 70° C. for 15 minutes, and then, the reaction was stopped. The amount of the cDNA synthesized by the reverse transcription reaction was quantified so that the effect of CspA was confirmed.

Figure 10:
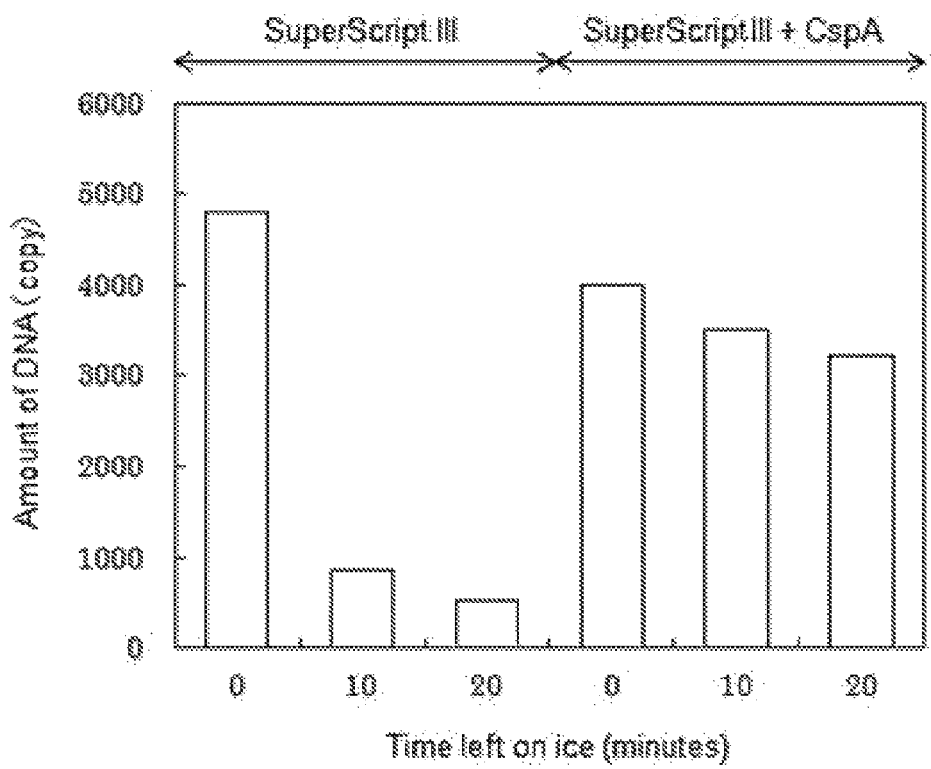
FIG. 10 is a drawing illustrating an effect exerted by CspA for improving reactivity of reverse transcription reaction.

As a result, in the reaction solution not including CspA, the amount of the long-stranded extension products from the vicinity of PolyA was reduced to 11% in the case where the solution was left on ice for 20 minutes in comparison to the solution not left on ice at all. In the reaction solution including CspA, the amount of the synthesized cDNA was 80% though it was left on ice for 20 minutes in comparison to the solution not left on ice at all (FIG. 10). It was confirmed that CspA could suppress the inhibition of the long-stranded cDNA synthesis reaction from the PolyA which results from the preparation of the reverse transcription reaction solution and leaving it on ice though SuperScript III RTase was used as the reverse transcriptase.

Example 11

Inhibition of Long-Stranded cDNA Synthesis Reaction in Reverse Transcription Reaction Wherein Oligo dT is Used as a Primer The test was performed according to a process similar to that of the example 9 except that 20 µL of a reverse transcription reaction solution including 1 µL of 1 µg/µL Human heart total RNA (manufactured by Clontech), 1 µL of 50 µM Oligo dT, 1.6 µL of each 2.5 mM dNTP mixture, 2 µL of Reverse Transcriptase XL (AMV) Buffer, 0.5 µL of 40 U/µL Ribonuclease Inhibitor, 0.8 µl, of 25 U/µL Reverse Transcriptase XL (AMV), and 1 µL of 2 µg/µL CspA and 20 µL of a reverse transcription reaction solution not including CspA were prepared using Reverse Transcriptase XL (AMV) (manufactured by TAKARABIO INC.) in place of PrimeScript (registered trademark) RTase. The amount of the cDNA synthesized by the reverse transcription reaction was quantified so that the effect of CspA was confirmed.

Figure 11:
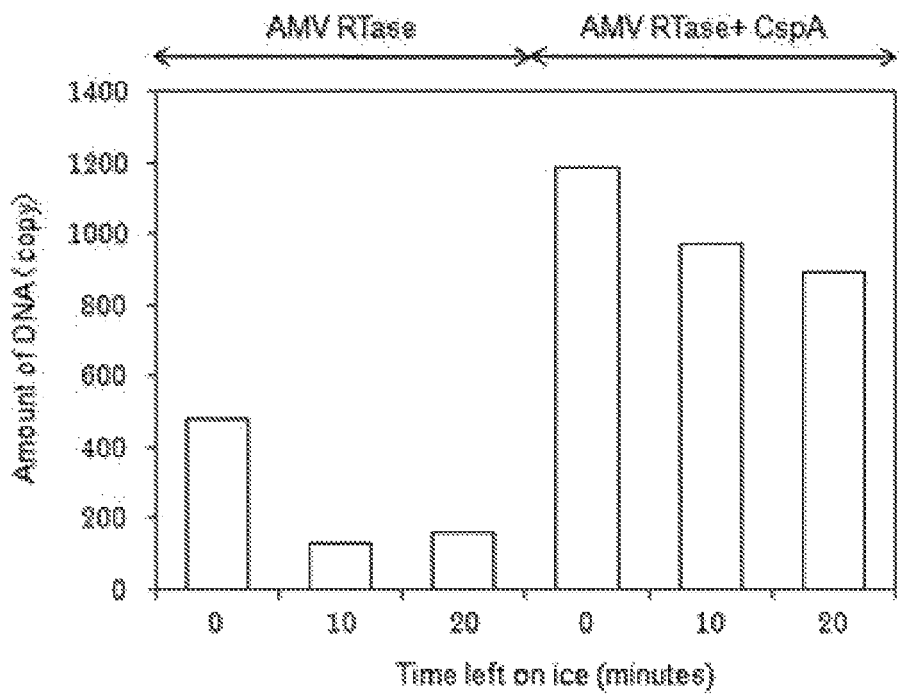
FIG. 11 is a drawing illustrating an effect exerted by CspA for improving reactivity of reverse transcription reaction.

As a result, in the reaction solution not including CspA, the amount of the long-stranded extension products from the vicinity of PolyA was reduced to 33% in the case where the solution was left on ice for 20 minutes in comparison to the solution not left on ice at all. In the reaction solution including CspA, the amount of the synthesized cDNA was 75% though it was left on ice for 20 minutes in comparison to the solution not left on ice at all (FIG. 11). It was confirmed that CspA could suppress the inhibition of the long-stranded cDNA synthesis reaction from the PolyA which results from the preparation of the reverse transcription reaction solution and though the reverse transcriptase derived from AMV was used as the reverse transcriptase.

Example 12

Effect of CspA Exerted on Reverse Transcription Reaction Using Native RNA as a Template The 5 µg/µL CspA solution prepared in the preparation example was diluted with an enzyme storage buffer so that a 0.2 µg/µL CspA solution, a 1 µg/µL CspA solution and a 2 µg/µL CspA solution were prepared. Next, each mixtures of 10 µL of total volume was respectively prepared in such a manner that 1 µL of the enzyme storage buffer, 0.2 µg/µL CspA solution, 1 µg/µL CspA solution, 2 µg/µL CspA solution or 5 µg/µL CspA solution were respectively added to 1 µL of 1 µg/µL Human heart total RNA (manufactured by Clontech), 1 µL of 50 µM Oligo dT, 1 µL of each 10 mM dNTP mixture, and 6 µL of sterilized distilled water. Referring to the mixture, which was not including CspA and prepared using the enzyme storage buffer, two different mixtures were prepared. One of such mixture was subjected to the RNA denature step at 65° C. for five minutes, and the other was not subjected such step. The RNA denature step was not performed to the mixtures including CspA.

Figure 12:
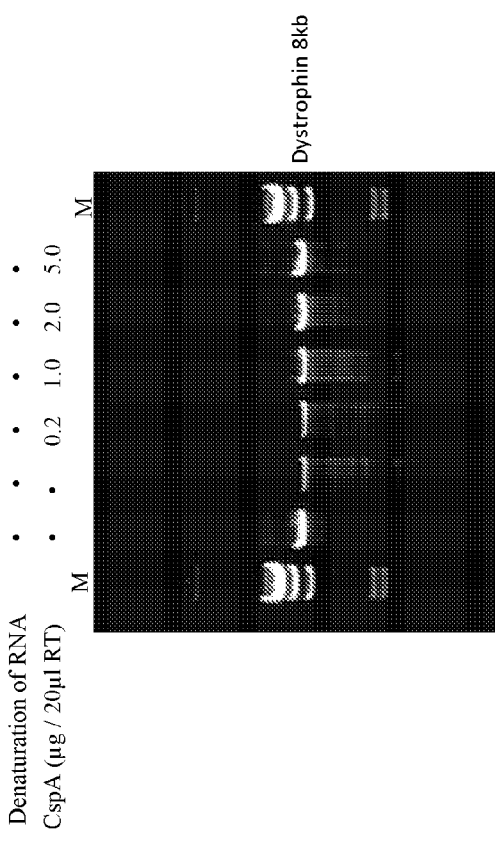
FIG. 12 is a drawing illustrating an effect exerted by CspA for improving reactivity of reverse transcription reaction. M in FIGS. 6 through 12 denotes a lane where 2.5 µL of λ-Hind III digest (manufactured by TAKARABIO INC.) marker was subjected to the electrophoresis.

4 µL of 5× PrimeScript Buffer included in PrimeScript 1st strand cDNA Synthesis Kit (manufactured by TAKARABIO INC.), 0.5 µL of 40 U/µL Ribonuclease Inhibitor, 0.5 µL of 200 U/µL PrimeScript RTase, and 5 µL of sterilized distilled water were added to 10 µL of these mixtures, so that 20 µL of the reaction solutions in total were prepared. The reaction solutions were then subjected to the reverse transcription reaction at 42° C. for 30 minutes and heated at 95° C. for five minute to stop the reaction. Next, 2.5 pit of these reaction solutions were subjected to a PCR which targets a region of approximately 8 kb in a dystrophin gene. TaKaRa LA Taq (registered trademark) Hot start Version (manufactured by TAKARABIO INC.) was used as the PCR, and the reaction was performed with the reaction composition recited in the instruction manual attached thereto. As the primer, a primer having the nucleotide sequence shown in SEQ ID NO: 20 and a primer having the nucleotide sequence shown in SEQ ID NO: 21 were used. The concentration of each primer in the PCR reaction solutions was 200 nM. Further, the PCR was performed by TaKaRa PCR Thermal Cycler Dice (registered trademark) (manufactured by TAKARABIO INC.) under the conditions of 30 cycles in which 98° C. for 10 seconds-68° C. for eight minutes constitutes one cycle. After the PCR reaction is completed, 3 µL of the reaction solutions were subjected to the agarose gel electrophoresis so that the strand lengths and the amount of amplification products were confirmed. Based on the confirmation, the amount of synthesized cDNA and the reaction specificity in each reverse transcription reaction were evaluated (FIG. 12).

As a result, the amount of amplified long-stranded cDNA of approximately 8 kb were largely increased, while the amount of amplified DNA in other than the target was reduced by analysis after PCR (FIG. 12) in the case of CspA was included in the reaction solution in the reverse transcription reaction wherein the native RNA was used as a template. It was shown from the result that the cDNA synthesis could be performed with a high efficiency and a high specificity when the CspA was added to the reaction solution, which makes the RNA denature step unnecessary.

Example 13

Effect of CspA Exerted on 1-Step RT-PCR

Figure 13:
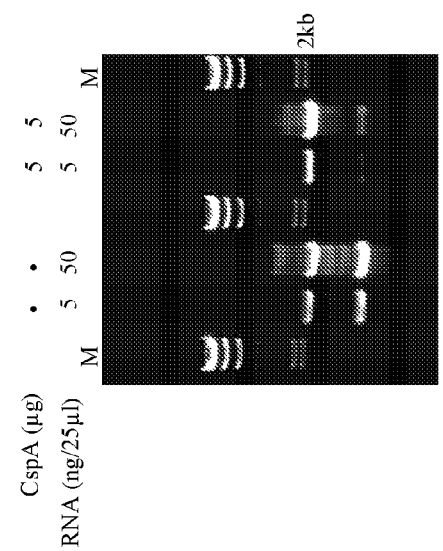
FIG. 13 is a drawing illustrating an effect exerted by CspA for improving reactivity of reverse transcription reaction. M in FIG. 13 denotes a lane where 2.5 µL of λ-Hind III digest (manufactured by TAKARABIO INC.) marker was subjected to the electrophoresis.

The 1-step RT-PCR which targets a region of approximately 2 kb in a dystrophin gene, wherein 5 ng or 50 ng Human heart total RNA (manufactured by Clontech) was used as a template, was performed using PrimeScript (registered trademark) One Step RT-PCR Kit (manufactured by TAKARABIO INC.). As the primer, a primer having the nucleotide sequence shown in SEQ ID NO: 21 and a primer having the nucleotide sequence shown in SEQ ID NO: 22 were used. Referring to the composition of a solution used in the 1-step RT-PCR, 5 µg CspA was added to 25 µL of the reaction solution whose composition was recited in the instruction manual attached to the PrimeScript (registered trademark) One Step RT-PCR Kit. Further, a reaction solution not including CspA to which 1 μL of the enzyme storage buffer was added in place of 5 μg CspA, and a reaction solution to which 1 μL of a Single-Stranded DNA Binding Protein (SSB) solution (manufactured by USB Corporation) (5 μg/μL SSB, 50 mM Tris-HCl (pH 7.5), 200 mM NaCl, 0.1 mM EDTA, 1 mM DTT, 50% glycerol) was added in place of 5 μg CspA were also prepared. These reaction solutions subjected to the reverse transcription reaction at 42° C. for 30 minutes and heated at 94° C. for two minutes, and then, the PCR reaction under the condition of 30 cycles in which 94° C. for 30 seconds-55° C. for 30 seconds-72° C. for two minutes constitute one cycle, was performed thereto using TaKaRa PCR Thermal Cycler dice (registered trademark). After the reaction was completed, 3 μL of the reaction solutions were subjected to the agarose gel electrophoresis so that reaction products were analyzed (FIG. 13).

As a result, the non-specific amplification products of any size other than the targeted size of approximately 2 kb were remarkably reduced in the solution including CspA. When SSB is added, the amplification products of the targeted size were not obtained.

Example 14

Effect of CspA in RT-PCR Reaction to Improve Yield and Specificity of the Reaction Human heart RNA was used as a template for the reaction and RT-PCR target was Dystrophin 2. Reactions were carried out in the presence of PrimeScript RTase, RNase inhibitor, ExTaq HS or PrimeStar Max, oligonucleotides. The duplicate reactions were carried out with or without CspA. Different temperatures such as 42° C. or 50° C. were also tested. It was observed, that in the presence of CspA, non-specific products were reduced and also the yield of the product improved with increase in the amount of CspA (up to 2.5 μg CspA per 10 □l reaction). CspA is also active at higher temperatures such as 42° C. and 50° C. The results with CspA were found to be comparable with reactions in which the secondary structures in the RNA were destabilized by heat treatment.

Example 15

(His)$_6$MazF-mt3 protein expressed from pET-28a-MazF-mt3 was purified with use of Ni-nitrilotriacetic acid resin. When purified MazF-mt3 was incubated with MS2 RNA in the absence of CspA, partial cleavage of the RNA was observed (lane 3) (FIG. 14B). As increasing amounts of CspA protein were added to the reaction mixture, the cleavage of the MS2 RNA substrate was enhanced (lanes 4 to 6). At the highest concentration of CspA no full-sized MS2 RNA was detected (lane 6). This concentration (0.86 mM) is 32 fold higher that the Kd value of CspA for RNA binding, indicating that the MS2 RNA was almost completely saturated with CspA, which binds every 6 bases of RNA. These results also demonstrate that MazF-mt3 is an mRNA interferase capable of cleaving single-stranded RNAs that are generated when CspA unfolds MS2 secondary structure.

Example 15

MazF-mt3 Specifically Cleaves RNA at CUCCU and UUCCU

Figure 15A:
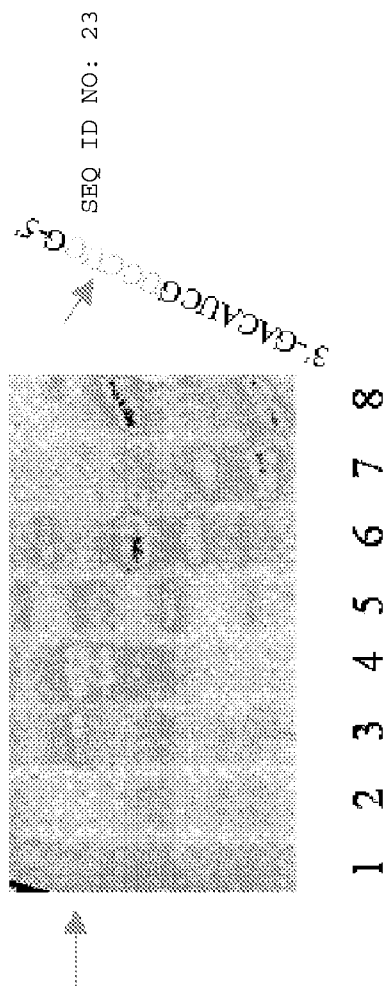
Figure 15B:
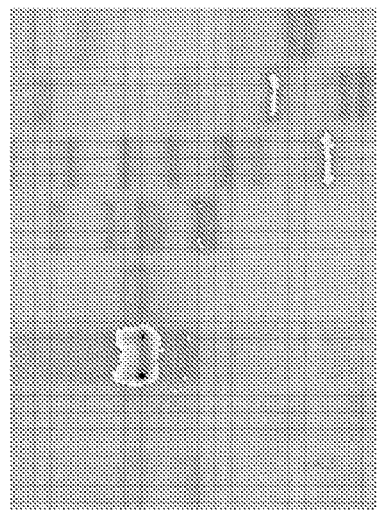
Figure 15D:
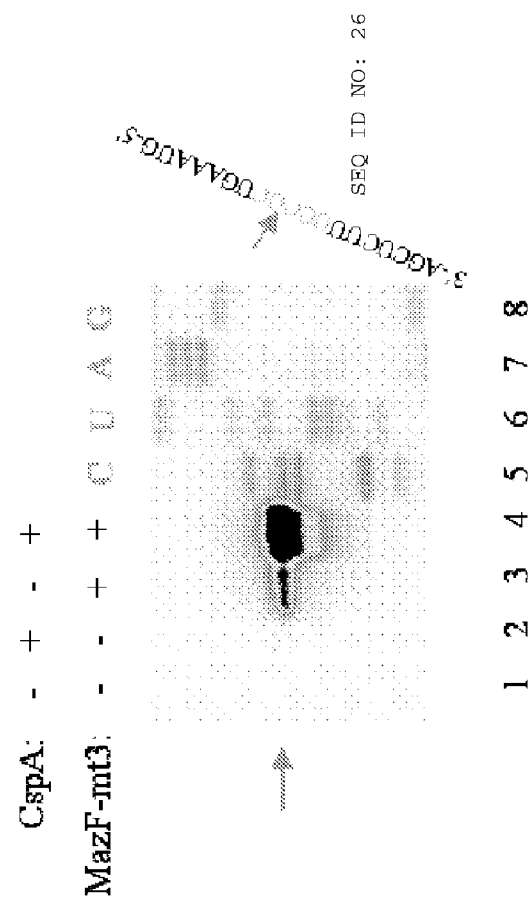
Figure 15F:
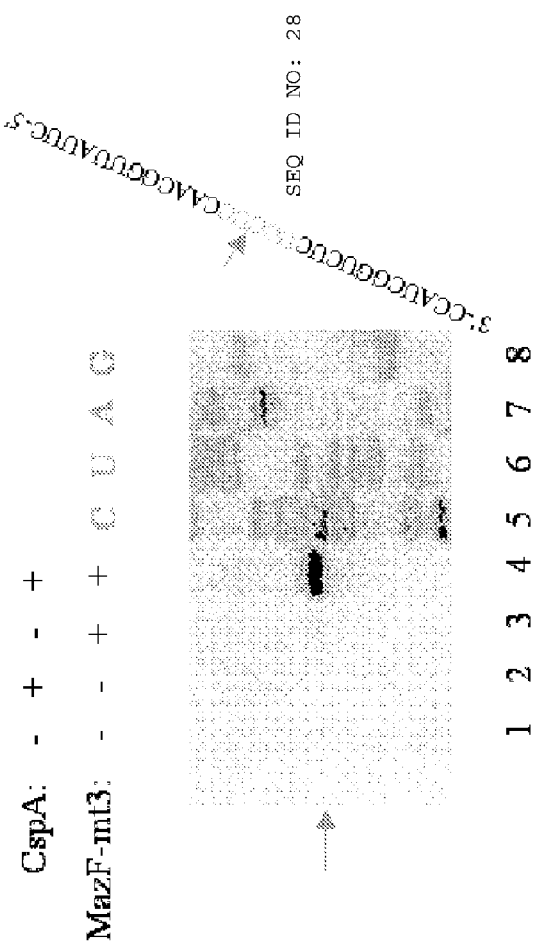
Figure 15H:
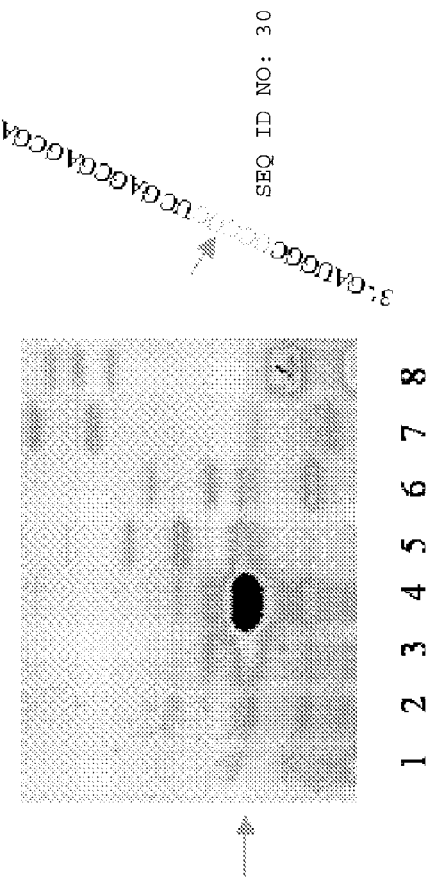

Primer extension experiments were carried out to determine the cleavage sites of MazF-mt3 in the MS2 RNA using the reaction mixture in the presence of 0.43 mM CspA. In order to cover the entire MS2 RNA sequence, a total of 22 primers were synthesized for the primer extension experiments. As shown in FIGS. 15A to H, in most cases the addition of CspA, significantly enhanced RNA cleavage. Notably, the RNA cleavage was detectable only in the presence of CspA for the cleavage site shown in FIG. 15F. The cleavage of the RNA at base 1028 (FIG. 15B) appears to be reduced in the presence of CspA, which is due to enhanced cleavage of a site at base 1078 immediately downstream of the cleavage site at base 1028, located between the primer binding site and the upstream cleavage site. This highly enhanced cleavage site at base 1078 in the presence of CspA is shown in FIG. 15C. Through these experiments, eight cleavage sites were identified, as listed in Table 2. The consensus sequence from these cleavage sites is CUCCU, where MazF-mt3 cleaves between the U residue in the second position and the C residue in the third position. Although we identified eight MazF-mt3 cleavage sites, there are nine CUCCU sequences in the MS2 RNA according to the published MS2 sequence (NCBI website). We therefore re-sequenced the region containing the ninth CUCCU sequence and found that there is no CUCCU sequence in the region. The MS2 RNA used in these experiments (Roche) contained CCUCU (base 2158 to base 2162) instead of CUCCU. Therefore, all the CUCCU sequences in MS2 RNA were cleaved by MazF-mt3.

Four other cleavage sites were detected which are different from those found in FIG. 15 as shown in FIGS. 16A to D. The consensus sequence from these primer extension experiments is UUCCU, where MazF-mt3 cleaves between the U residue in the second position and the C residue in the third position. There are five UUCCU sequence in the MS2 RNA all of which were confirmed by RNA sequence. All the cleavage sites for MazF-mt3 are shown by arrows in FIG. 1A.

Example 16

MazF-Mt7 is Also a Sequence-Specific mRNA Interferase

Figure 17B:
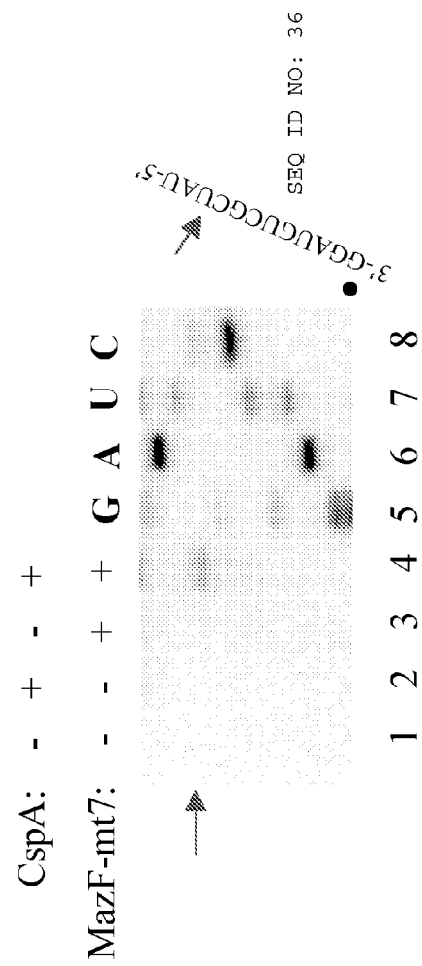
Figure 17D:
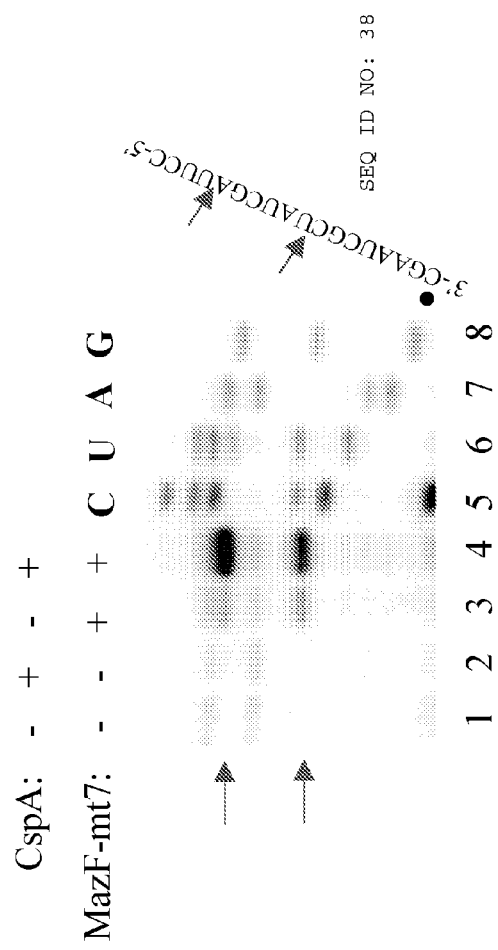
Figure 17E:
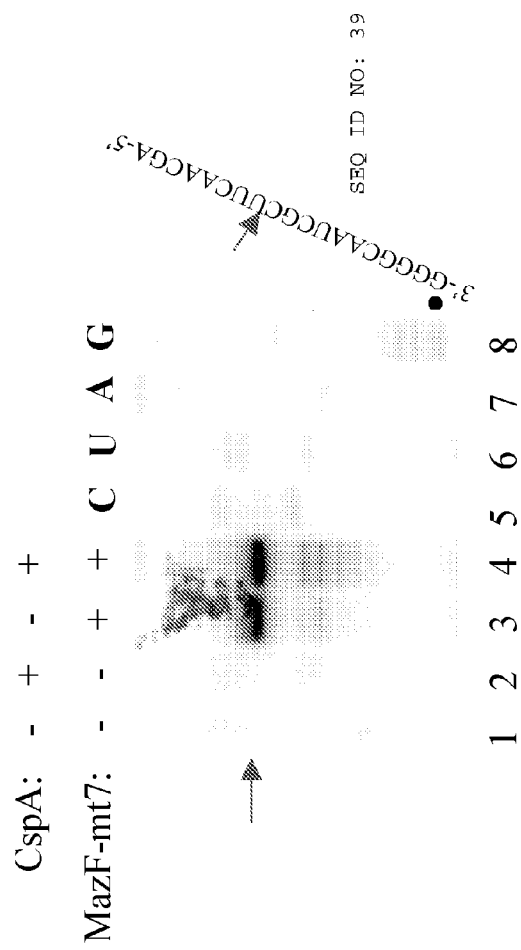
Figure 17F:
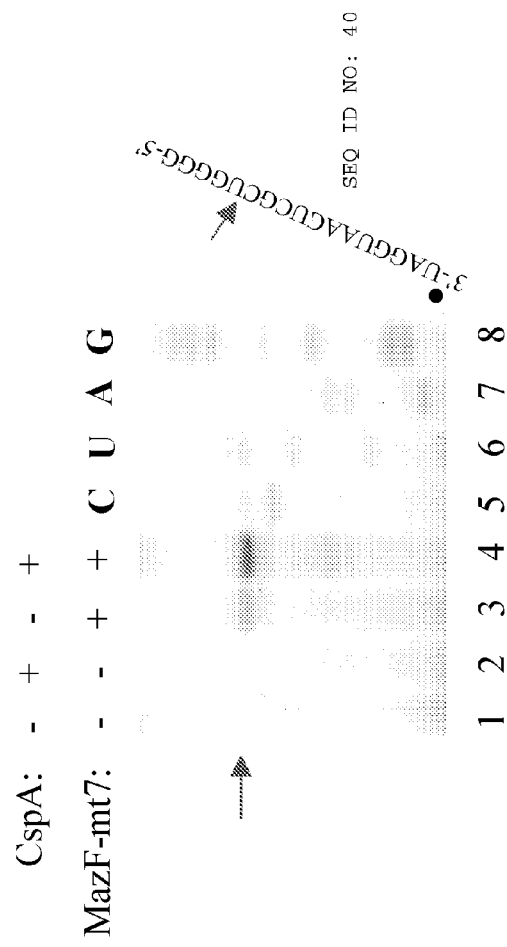
Figure 17G:
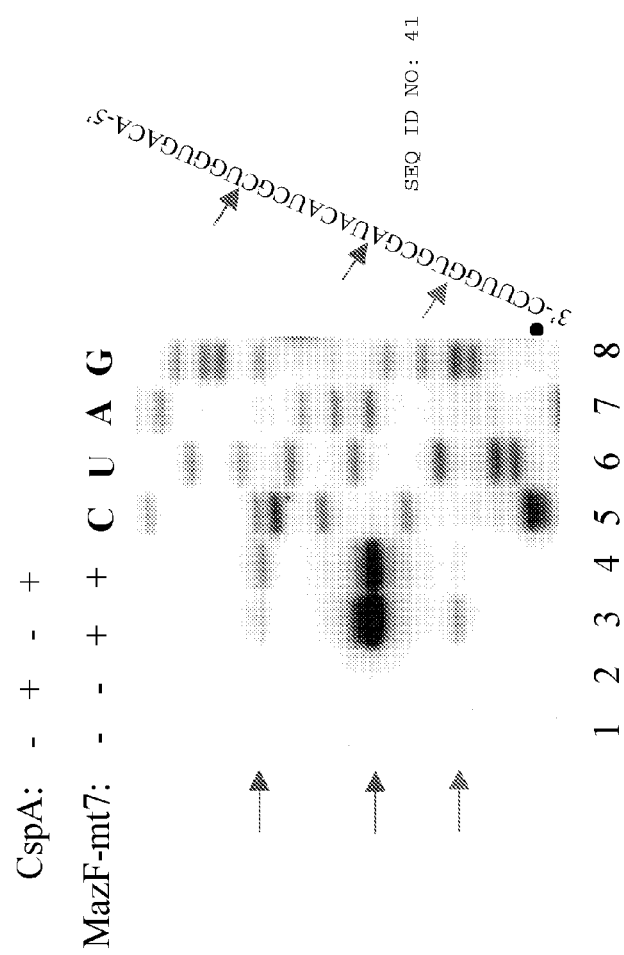
Figure 17H:
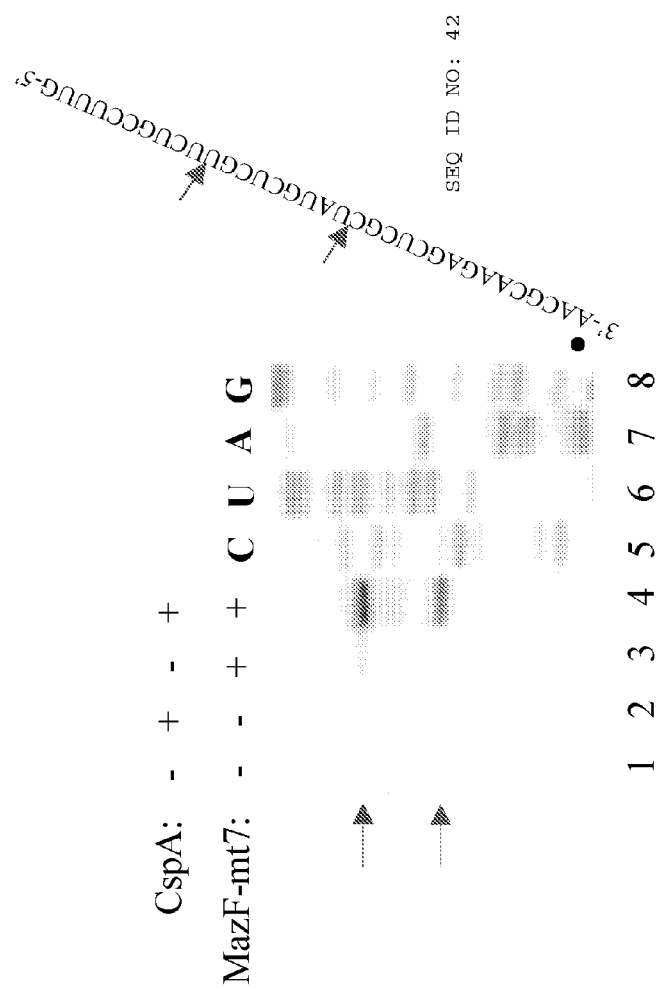
Figure 17I:
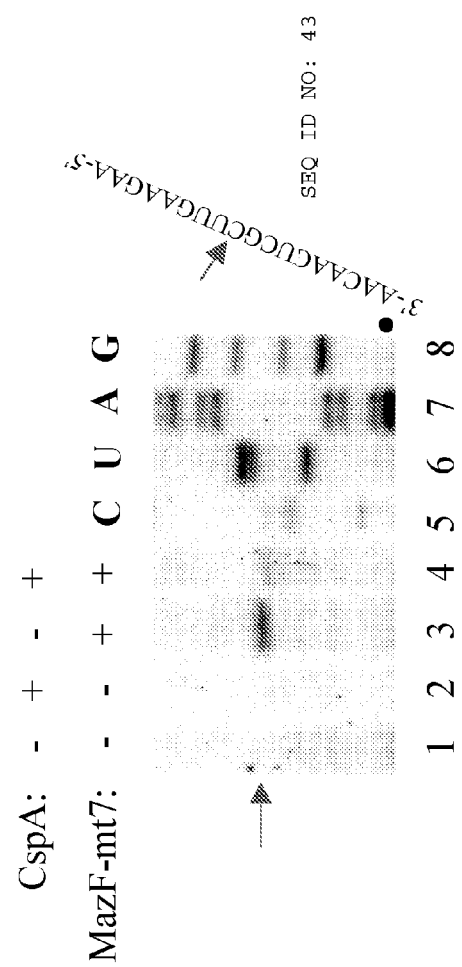
Figure 17J:
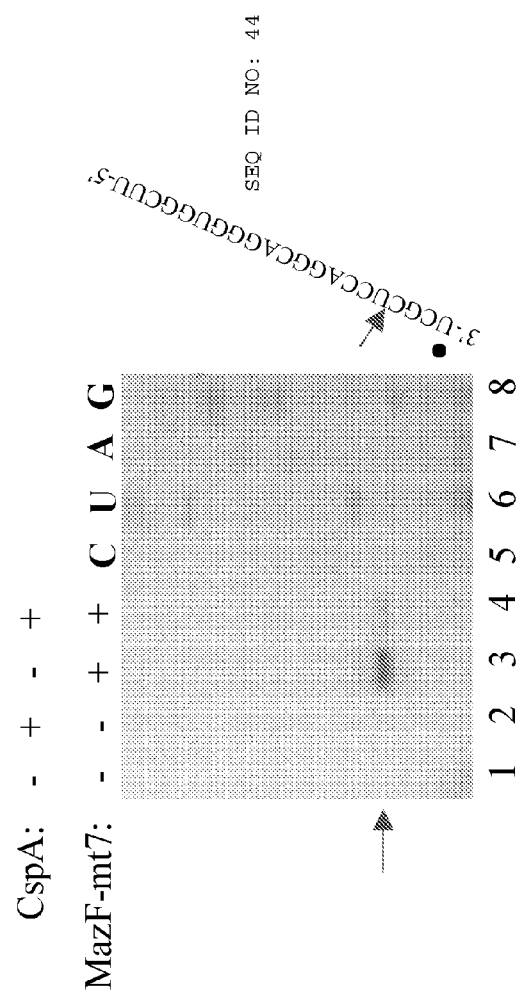
Figure 17K:
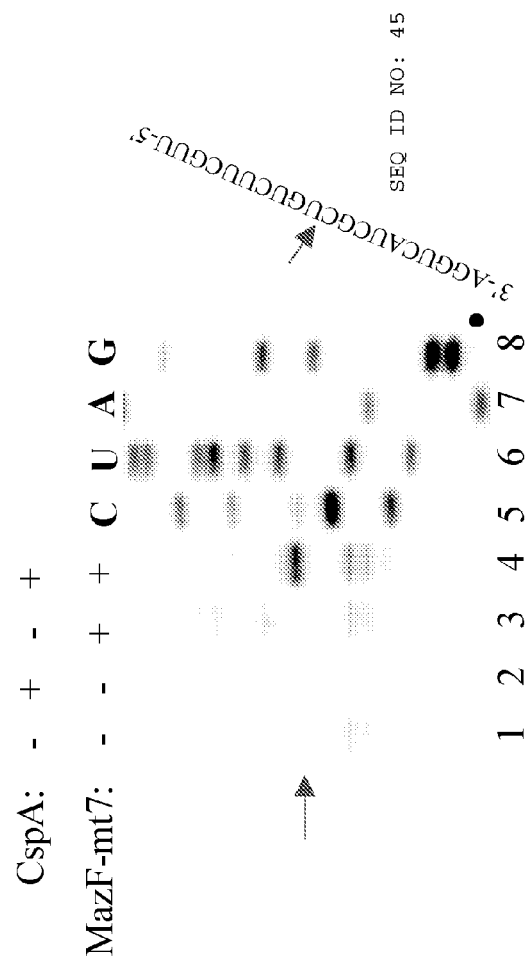
Figure 17L:
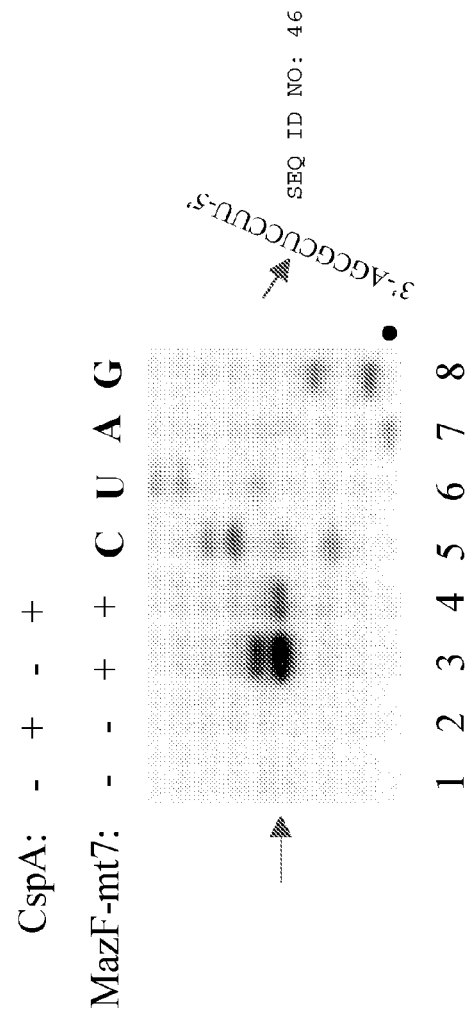
Figure 17M:
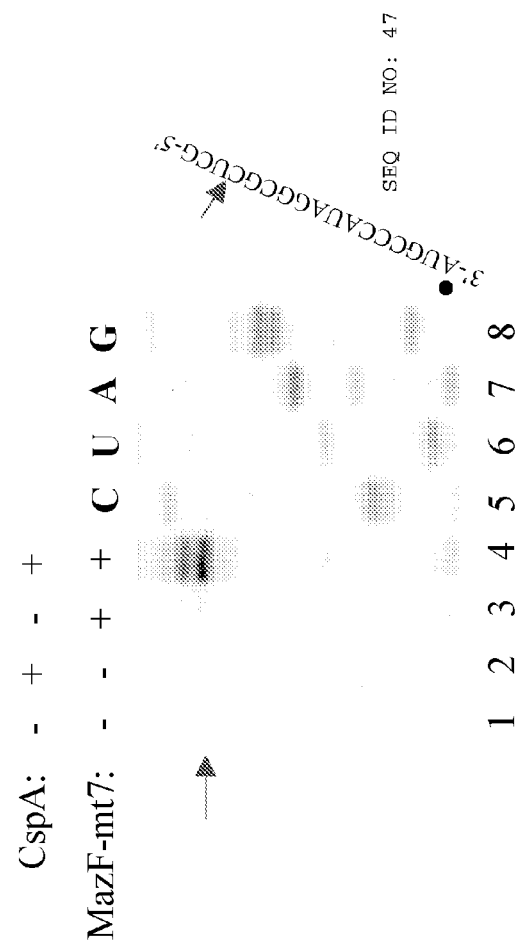
Figure 17N:
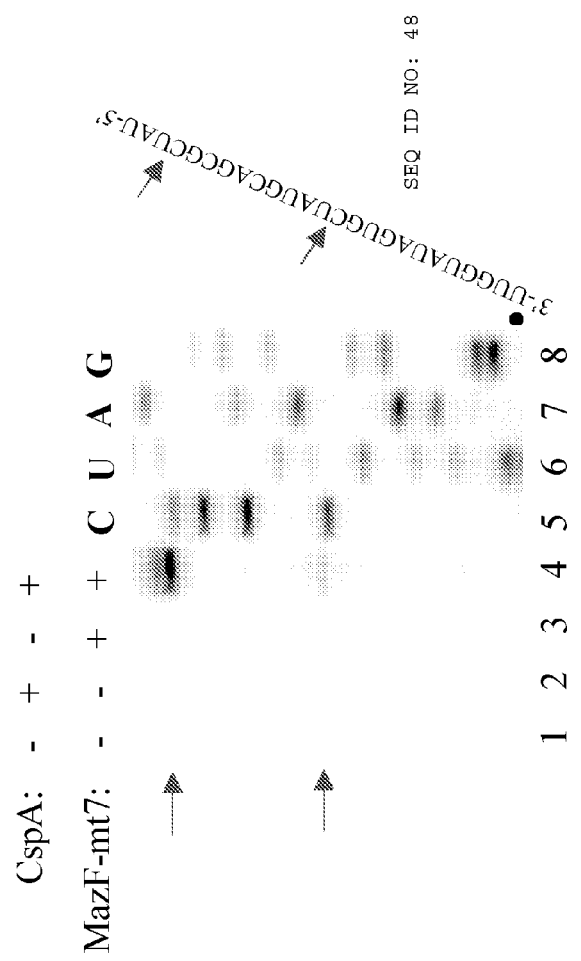
Figure 17O:
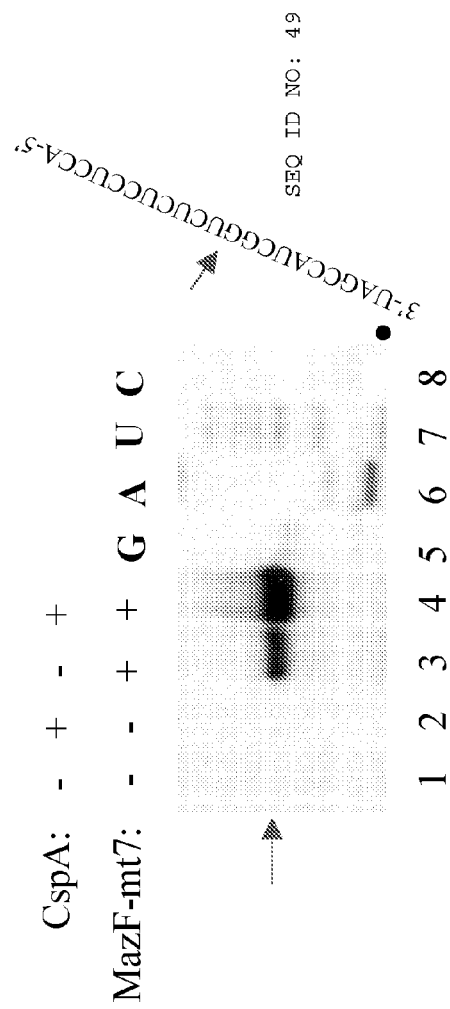
Figure 17P:
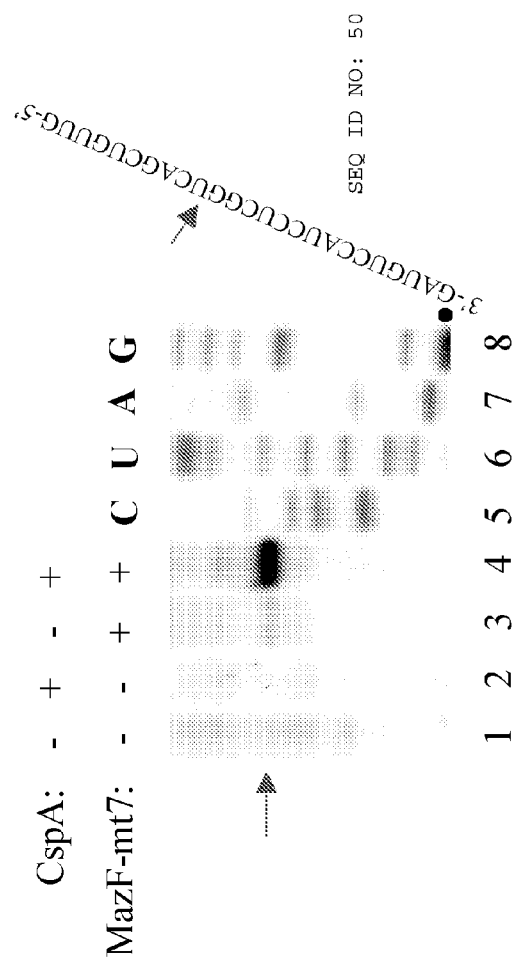
Figure 17Q:
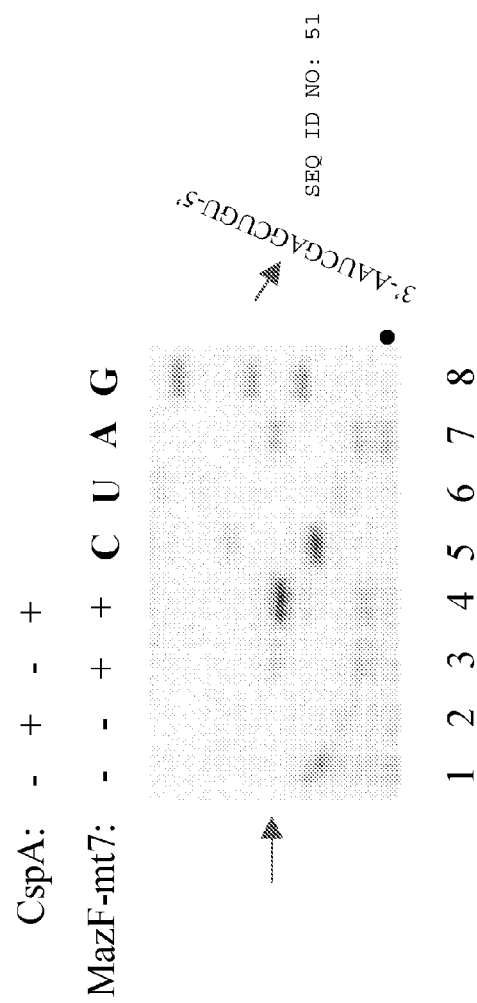

The MS2 RNA-CspA system described herein was used to identify the specific cleavage sites of MazF-mt7. Using purified N-terminal His-tagged MazF-mt7, primer extension experiments were carried out and the results are shown in FIGS. 17A to R and summarized in Table 3. Most of the cleavage sites contain the sequence UCGCU (FIGS. 17A-K), where MazF-mt7 cleaves between first U and second C. Some of cleavage sites have a one-base mismatch from the consensus UCGCU (FIGS. 17 C, D, H and L-P), and a few cleavage sites with two-base mismatch (FIGS. 17 G, N, Q, R). All these cleavage sites, however, share the central G residue and most of them also have a C residue following the central G residue. MazF-mt7 was thus found to be an mRNA interferase that recognizes a five-base U'CGCU sequence; however it appears to be less stringent than MazF-mt3.

Example 17

Primer Extension Analysis In Vitro

For primer extension analysis of mRNA cleavage sites in vitro, the full-length MS2 mRNAs were partially digested with or without purified toxin protein (MazF-mt3 or MazF-mt7), and with or without purified CspA protein at 37° C. for 15 min. The digestion reaction mixture (10 μl) consisted of 0.8 µg of MS2 RNA substrate, 0.0625 µg of MazF-mt3(His)$_6$ or MazF-mt7(His)$_6$, 321 µg CspA and 0.5 µl of RNase inhibitor (Roche) in 10 mM Tris-HCl (pH 7.8). Primer extension was carried out at 47° C. for 1 h in 20 µl of the reaction mixture. The reactions were stopped by adding 12 µl of sequence loading buffer (95% formamide, 20 mM EDTA, 0.05% bromphenol blue, and 0.05% xylene cyanol EF). The samples were incubated at 90° C. for 5 min prior to electrophoresis on a 6% polyacrylamide and 36% urea gel. The primers used for primer extension analysis of the MS2 mRNA are listed in Table 1. The primers were 5'-labeled with [γ-$^{32}$P]ATP using T4 polynucleotide kinase.

TABLE 1

Primers used in the Primer Extension

| Primer Name | Sequence | Primer Name | Sequence |
|---|---|---|---|
| B3 SEQ ID NO: 53 | 5'-AGCACACCCACCCCGTTTAC-3' | E SEQ ID NO: 64 | 5'-GAAGATCAATACATAAAGAG-3' |
| B4 SEQ ID NO: 54 | 5'-GGTCCGTCCCACCGAAGAAC-3' | E1 SEQ ID NO: 65 | 5'-TGCATTGCCTTAACAATAAG-3' |
| B5 SEQ ID NO: 55 | 5'-AGAACTTGCGTTCTCGAGCG-3' | E2 SEQ ID NO: 66 | 5'-TACAGGTTACTTTGTAAGCC-3' |
| B7 SEQ ID NO: 56 | 5'-TATAACGCGCACGCCGGCGG-3' | G SEQ ID NO: 67 | 5'-GAGCCGTTGCCTGATTAATG-3' |
| B8 SEQ ID NO: 57 | 5'-CGGAGTCTTGGTGTATACCG-3' | H SEQ ID NO: 68 | 5'-AGCGTCAACGCTTATGATGG-3' |
| C2 SEQ ID NO: 58 | 5'-GCGGATACGATCGAGATATG-3' | I SEQ ID NO: 69 | 5'-AGCATCCCACGGGGCCG-3' |
| C3 SEQ ID NO: 59 | 5'-GCGCACATTGGTCTCGGACC-3' | J SEQ ID NO: 70 | 5'-GGTTCAAGATACCTAGAGAC-3' |
| D SEQ ID NO: 60 | 5'-CCGCTCTCAGAGCGCGGGGG-3' | J1 SEQ ID NO: 71 | 5'-GACGGCCATCTAACTTGATG-3' |
| D1 SEQ ID NO: 61 | 5'-GCAATTGATTGGTAAATTTC-3' | K1 SEQ ID NO: 72 | 5'-CTTCGGTCGACGCCCGGTTC-3' |
| D2 SEQ ID NO: 62 | 5'-TCTCTATTTATCTGACCGCG-3' | L1 SEQ ID NO: 73 | 5'-TAGCCATGGTAGCGTCTCGC-3' |
| D5 SEQ ID NO: 63 | 5'-AATTCGTCCCTTAAGTAAGC-3' | L2 SEQ ID NO: 74 | 5'-CCTATCAAGGGTACTAAAAG-3' |

TABLE 2

Cleavage sites of MazF-mt3 in MS2 RNA

| Cleavage site: CU↓CCU | Cleavage site: UU↓CCU |
|---|---|
| CUT 0426 0430 (SEQ ID 75) ACG CU↓CCU GCU | 0032 0036 (SEQ ID 83) AAC UU↓CCU GUC |
| 1027 1031 (SEQ ID 76) UGG CU↓CCU ACC | 0111 0115 (SEQ ID 84) CCA UU↓CCU AGG |
| 1077 1081 (SEQ ID 77) A[[T]]UG CU↓CCU ACA | 0806 0810 (SEQ ID 85) UUC UU↓CCU A[[T]]UG |
| 1247 1251 (SEQ ID 78) AGU CU↓CCU UUC | 1567 1571 (SEQ ID 86) AGU UU↓CCU GUA |
| 1268 1272 (SEQ ID 79) GGU CU↓CCU AAA | |
| 2103 2107 (SEQ ID 80) AAC CU↓CCU CUC | |
| 3056 3060 (SEQ ID 81) GCU CU↓CCU CCC | |

TABLE 2-continued

Cleavage sites of MazF-mt3 in MS2 RNA

| Cleavage site: CU↓CCU | Cleavage site: UU↓CCU |
|---|---|
| 3388  3392<br>(SEQ ID 82) GCU CU↓CCU CGG | |
| NOT CUT | 1804  1808<br>(SEQ ID 87) AUC UUCCU CGC | a: The numbers in the table represent the base number of MS2 RNA

TABLE 3

Cleavage sites of MazF-mt7 in MS2 RNA

| Cleavage sites<br>U↓CGCU | One-base difference<br>from the U↓CGCU sequence | Two-bases difference<br>From the U↓CGCU sequence |
|---|---|---|
| 1621  1625 (SEQ ID 88)<br>AAUUU U↓CGCU ACGAA | 1808  1812 (SEQ ID 99)<br>CUUCC U↓CGCG AUCUU | 0911  0915 (SEQ ID 107)<br>ACGUA U↓CGUG AUAUG |
| 0087  0091 (SEQ ID 89)<br>GGCUA U↓CGCU GUAGG | 3172  3176 (SEQ ID NO 100)<br>GCUGC U↓CGCG GAUAC | 0040  0044 (SEQ ID 108)<br>CUGUC G↓AGCU AAUGC |
| 2517  2521 (SEQ ID 90)<br>AUGGU U↓CGCU UGCGA | 0901  0905 (SEQ ID 101)<br>ACAUA U↓CGCG ACGUA | 3383  3387 (SEQ ID 109)<br>CCAGC G↓AGCU CUCCU |
| 1978  1982 (SEQ ID 91)<br>AGCUA U↓CGCU AAGCU | 2111  2115 (SEQ ID 102)<br>CUCUC U↓GGCU ACCGA | 3262  3266 (SEQ ID 110)<br>CUACA U↓AGCG UGGUU |
| 1421  1425 (SEQ ID 92)<br>CAACU U↓CGCU AACGG | 1024  1028 (SEQ ID 103)<br>UCGAC U↓GGCU CCUAC | U { CGUG*<br>    AGCG |
| 1433  1437 (SEQ ID 93)<br>CGGGG U↓CGCU GAAUG | 2491  2495 (SEQ ID 104)<br>GCGUC U↓AGCU CAGCA | G { AGCU |
| 3254  3258 (SEQ ID 94)<br>AGUGG U↓CGCU ACAUA | 1972  1976 (SEQ ID 105)<br>UACCU U↓AGCU AUCGC | |
| 3211  3215 (SEQ ID 95)<br>UCGUA U↓CGCU CGAGA | 3202  3206 (SEQ ID 106)<br>CCGUC U↓UGCU CGUAU | |
| 1849  1853 (SEQ ID 96)<br>UUCUG U↓CGCU ACUGG | U { C  } GCG*<br>    U<br>    A  } GCU<br>    G | |
| 2203  2207 (SEQ ID 97)<br>GAAGU U↓CGCU GAACA | | |
| 3097  3101 (SEQ ID 98)<br>GGACC U↓CGCU GCCGA<br>      UCGCU* | | |

*: Consensus Sequence

What is claimed:

1. A composition for DNA synthesis comprising a cold shock protein A (CspA) protein of *Escherichia coli*; and a thermostable DNA polymerase, wherein the composition comprises more than 0.5 µg of the CspA protein per 25 µL of the composition.

2. The composition according to claim 1, further comprising at least one additional DNA polymerase.

3. The composition according to claim 2, wherein at least one DNA polymerase possesses 3'→5' exonuclease activity and at least one DNA polymerase possesses substantially no 3'→5' exonuclease activity.

4. The composition according to claim 1, further comprising at least one primer and at least one deoxyribonucleotide.

5. The composition according to claim 4, wherein the deoxyribonucleotide comprises a deoxyribonucleotide triphosphate.

6. The composition according to claim 4, further comprising a liquid vehicle.

7. The composition according to claim 6 wherein the liquid vehicle comprises a reaction buffer solution.

8. A composition for reverse transcription reaction comprising:
 a CspA protein of *Escherichia coli*; and
 a reverse transcriptase of Moloney Murine Leukemia Virus or Avian Myeloblastosis Virus,
 wherein the CspA protein is present in the composition at a concentration ranging from about 0.5 µg to about 20 µg of the CspA protein per 20 µL of the composition.

9. The composition according to claim 8, further comprising at least one primer and at least one deoxyribonucleotide.

10. The composition of claim 9, further comprising a liquid vehicle.

11. The composition of claim 10, wherein the liquid vehicle comprises a reaction buffer solution.

12. The composition of claim 9, further comprising an oligo (dT) primer or an oligonucleotide primer having a random sequence or a combination thereof.

* * * * *